United States Patent
Yamamoto

(10) Patent No.: US 11,064,864 B2
(45) Date of Patent: Jul. 20, 2021

(54) PROCESSOR DEVICE, ENDOSCOPE SYSTEM, AND METHOD OF OPERATING PROCESSOR DEVICE

(71) Applicant: FUJIFILM Corporation, Tokyo (JP)

(72) Inventor: Hiroaki Yamamoto, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 61 days.

(21) Appl. No.: 16/372,423

(22) Filed: Apr. 2, 2019

(65) Prior Publication Data

US 2019/0223690 A1 Jul. 25, 2019

Related U.S. Application Data

(63) Continuation of application No. PCT/JP2017/032720, filed on Sep. 11, 2017.

(30) Foreign Application Priority Data

Oct. 5, 2016 (JP) .............................. JP2016-197142

(51) Int. Cl.
*G06K 9/00* (2006.01)
*A61B 1/00* (2006.01)
(Continued)

(52) U.S. Cl.
CPC ...... *A61B 1/00009* (2013.01); *A61B 1/00045* (2013.01); *A61B 1/045* (2013.01);
(Continued)

(58) Field of Classification Search
None
See application file for complete search history.

(56) References Cited

U.S. PATENT DOCUMENTS 10,426,318 B2 * 10/2019 Kamon .................... A61B 1/00
10,653,295 B2 * 5/2020 Ebata .................... A61B 5/1459
(Continued)

FOREIGN PATENT DOCUMENTS

JP 2009148499 7/2009
JP 2012152279 8/2012
(Continued)

OTHER PUBLICATIONS

"Search Report of Europe Counterpart Application", dated Oct. 30, 2019, p. 1-p. 9.
(Continued)

*Primary Examiner* — Soo Jin Park
(74) *Attorney, Agent, or Firm* — JCIPRNET

(57) ABSTRACT

Provided are a processor device, an endoscope system, and a method of operating a processor device capable of narrowing down a plurality of index values to the index value required to diagnose a lesion. An image obtained by imaging an observation target including a structure is acquired. An index value calculation unit 70 performs an index value calculation process of calculating a plurality of index values obtained by indexing a property of the structure on the basis of the image. An index value arithmetic processing unit 74 controls the index value calculation unit 70 according to a processing order in which a first index value is calculated and then a second index value different from the first index value is calculated among the plurality of index values.

19 Claims, 15 Drawing Sheets

| | PROCESSING ORDER |
|---|---|
| DIAGNOSTIC PATTERN FOR ESOPHAGEAL CANCER | PROCESSING ORDER FOR ESOPHAGEAL CANCER |
| FIRST DIAGNOSTIC PATTERN FOR COLORECTAL CANCER | FIRST PROCESSING ORDER FOR COLORECTAL CANCER |
| SECOND DIAGNOSTIC PATTERN FOR COLORECTAL CANCER | SECOND PROCESSING ORDER FOR COLORECTAL CANCER |
| THIRD DIAGNOSTIC PATTERN FOR COLORECTAL CANCER | THIRD PROCESSING ORDER FOR COLORECTAL CANCER |
| ⋮ | ⋮ |

(51) Int. Cl.
  *A61B 1/045* (2006.01)
  *A61B 1/06* (2006.01)
  *G06T 1/00* (2006.01)
  *G02B 23/24* (2006.01)
  *G16H 30/40* (2018.01)

(52) U.S. Cl.
  CPC .............. *A61B 1/0676* (2013.01); *G06T 1/00* (2013.01); *A61B 1/00066* (2013.01); *G02B 23/24* (2013.01); *G16H 30/40* (2018.01)

(56) References Cited

U.S. PATENT DOCUMENTS

| | | |
|---|---|---|
| 2012/0089016 A1 | 4/2012 | Mizuno |
| 2012/0190922 A1 | 7/2012 | Kaku |
| 2013/0208958 A1 | 8/2013 | Tomoto |
| 2015/0193929 A1* | 7/2015 | Ikemoto ................. A61B 5/061 382/128 |
| 2015/0265222 A1 | 9/2015 | Sakaguchi |
| 2017/0112355 A1* | 4/2017 | Hirota .................... A61B 1/045 |
| 2017/0258296 A1 | 9/2017 | Kaku |
| 2019/0192048 A1* | 6/2019 | Making .................... G06T 1/00 |

FOREIGN PATENT DOCUMENTS

| | | | |
|---|---|---|---|
| JP | 2016016185 A * | 2/2016 | ........... A61B 5/0071 |
| JP | 2016144626 | 8/2016 | |
| WO | 2013008526 | 1/2013 | |
| WO | 2014064702 | 5/2014 | |
| WO | 2016006389 | 1/2016 | |
| WO | 2016121811 | 8/2016 | |

OTHER PUBLICATIONS

"Office Action of Japan Counterpart Application," with English translation thereof, dated Nov. 26, 2019, p. 1-p. 6.

"International Search Report (Form PCT/ISA/210) of PCT/JP2017/032720," dated Nov. 21, 2017, with English translation thereof, pp. 1-4.

"International Preliminary Report on Patentability (Form PCT/IPEA/409) of PCT/JP2017/032720," completed on Sep. 26, 2018, with English translation thereof, pp. 1-16. w.

* cited by examiner

FIG. 11

|  | PROCESSING ORDER |
| --- | --- |
| DIAGNOSTIC PATTERN FOR ESOPHAGEAL CANCER | PROCESSING ORDER FOR ESOPHAGEAL CANCER |
| FIRST DIAGNOSTIC PATTERN FOR COLORECTAL CANCER | FIRST PROCESSING ORDER FOR COLORECTAL CANCER |
| SECOND DIAGNOSTIC PATTERN FOR COLORECTAL CANCER | SECOND PROCESSING ORDER FOR COLORECTAL CANCER |
| THIRD DIAGNOSTIC PATTERN FOR COLORECTAL CANCER | THIRD PROCESSING ORDER FOR COLORECTAL CANCER |
| ⋮ | ⋮ |

PROCESSOR DEVICE, ENDOSCOPE SYSTEM, AND METHOD OF OPERATING PROCESSOR DEVICE

CROSS REFERENCE TO RELATED APPLICATIONS

This application is a Continuation of PCT International Application No. PCT/JP2017/032720 filed on Sep. 11, 2017, which claims priority under 35 U.S.C § 119(a) to Patent Application No. 2016-197142 filed in Japan on Oct. 5, 2016, all of which are hereby expressly incorporated by reference into the present application.

BACKGROUND OF THE INVENTION

1. Field of the Invention

The present invention relates to a processor device, an endoscope system, and a method of operating a processor device, which calculate index values obtained by indexing shape features and the like of a vascular pattern.

2. Description of the Related Art

In the medical field, diagnosis using an endoscope system comprising a light source device, an endoscope, and a processor device has been performed widely. The endoscope system irradiates an observation target via the endoscope with illumination light from the light source device, and the processor device produces an image of the observation target on the basis of an image signal obtained by capturing the observation target under illumination with the illumination light. By displaying the image on a monitor, a doctor can perform diagnosis while viewing this image on the monitor.

In endoscopic diagnosis, since vascular patterns or glandular patterns of a lesion have a specific shape and color, the vascular patterns or glandular patterns are classified by each of a shape and color to diagnose a type and a progress of the lesion (refer to FIG. 7 and the like). Since a certain amount of experience is accumulated in the diagnosis based on shapes such as the vascular patterns, in JP2012-152279A, a diagnosis support for determining progress of a lesion is performed by performing a pattern matching process using a vascular pattern.

In addition, since shapes such as vascular patterns are various, in WO2013/008526A, by associating the shapes such as vascular patterns with basic shapes of a straight line, a circle, and the like, the shapes such as the vascular patterns are easily quantified. Furthermore, as disclosed in JP2016-144626A, diagnosing a lesion is also performed by using an index value obtained by indexing properties of various structures such as a blood vessel density and a blood vessel thickness. In JP2016-144626A, shapes of vascular patterns or the like are indexed as an index value, and a type and a progress of the lesion are determined from the obtained index value.

SUMMARY OF THE INVENTION

As disclosed in JP2016-144626A, in a case where diagnosing the lesion is performed using a plurality of index values, unnecessary index values for diagnosis of the lesion may be included in a plurality of index values depending on the type and the progress of the lesion. For example, in a case of observing a vascular pattern having a possibility to be progressed to a high-grade lesion, an index value of a specific vascular pattern in a case where a progress of a lesion is low is more likely to be unnecessary. In such a case, there is a concern that an analysis efficiency of the index values is reduced, and the inspection time is wasted. Therefore, it is desired to efficiently perform a diagnosis using an index value by narrowing down the plurality of index values to an index value required to diagnose the lesion.

An object of the invention is to provide a processor device, an endoscope system, and a method of operating a processor device capable of narrowing down a plurality of index values to an index value required to diagnose a lesion.

A processor device comprises an image acquisition unit that acquires an image obtained by imaging an observation target including a structure; an index value calculation unit that performs an index value calculation process of calculating a plurality of index values obtained by indexing a property of the structure on the basis of the image; a processing order storage unit that stores a processing order in which a first index value is calculated and then a second index value different from the first index value is calculated among the plurality of index values; and an index value arithmetic processing unit that controls the index value calculation unit to perform the index value calculation process according to the processing order.

The processor device further comprises an index value determination unit that performs an index value determination process of determining the index value on the basis of a reference corresponding to the index value. The index value arithmetic processing unit controls the index value calculation unit and the index value determination unit to perform a first index value arithmetic process of calculating the first index value among the plurality of index values, a first index value determination process of determining the first index value on the basis of a reference for the first index value, and a second index value calculation process of selecting the second index value among the plurality of index values according to a result of the first index value determination process and calculating a selected second index value.

It is preferable that the processor device further comprises a mucous membrane determination unit that performs a mucous membrane determination process of determining a state of a mucous membrane on the basis of an index value for mucous membrane determination. The index value arithmetic processing unit performs a control so as to repeat the index value calculation process until a calculation of the index value for mucous membrane determination is completed. It is preferable that the state of the mucous membrane includes a type of a lesion, a progress of a lesion, and a normal mucous membrane state. It is preferable that the structure includes a blood vessel structure or a mucous membrane structure. It is preferable that the image acquisition unit acquires a multi-frame image obtained by imaging the observation target in different frames, the multi-frame image including an image for index value calculation. It is preferable that the processing order is preset on the basis of medical knowledge for the specific lesion.

An endoscope system of the invention comprises the processor device of the invention described above; a display unit that displays an index value image obtained by imaging the index value; and a display control unit that performs a display control according to the processing order so that the first index value is displayed on the display unit and then the second index value is displayed on the display unit. An endoscope system of the invention comprises the processor device of the invention described above and a display unit that displays a result of the mucous membrane determination process.

A processor device of the invention comprises an image acquisition unit that acquires an image obtained by imaging an observation target including a structure; an index value calculation unit that performs an index value calculation process of calculating index values obtained by indexing a property of the structure on the basis of the image; an index value determination unit that performs an index value determination process of determining the index value on the basis of a reference corresponding to the index value; a processing order storage unit that stores a processing order in which a first index value is calculated and then a second index value different from the first index value is calculated among the plurality of index values; and an index value arithmetic processing unit that controls the index value calculation unit to perform the index value calculation process according to the processing order. The index value arithmetic processing unit controls the index value calculation unit and the index value determination unit to perform a first index value arithmetic process of calculating the first index value, a first index value determination process of determining the first index value on the basis of a reference for the first index value, and a second index value calculation process of selecting the second index value among the plurality of index values according to the result of the first index value determination process and calculating a selected second index value.

A method of operating a processor device of the invention comprises a step of acquiring an image obtained by imaging an observation target including a structure, using an image acquisition unit; a step of performing an index value calculation process of calculating a plurality of index values obtained by indexing a property of the structure on the basis of the image, using an index value calculation unit; and a step of controlling the index value calculation unit to perform the index value calculation process according to a processing order in which a first index value is calculated and then a second index value different from the first index value is calculated among a plurality of index values, using an index value arithmetic processing unit.

According to the invention, it is possible to narrow down a plurality of index values to an index value required to diagnose a lesion.

BRIEF DESCRIPTION OF THE DRAWINGS

FIG. 11 is a table showing a processing order for an index value calculation process and an index value determination process stored in a processing order storage unit.

DESCRIPTION OF THE PREFERRED EMBODIMENTS

First Embodiment

Figure 1:
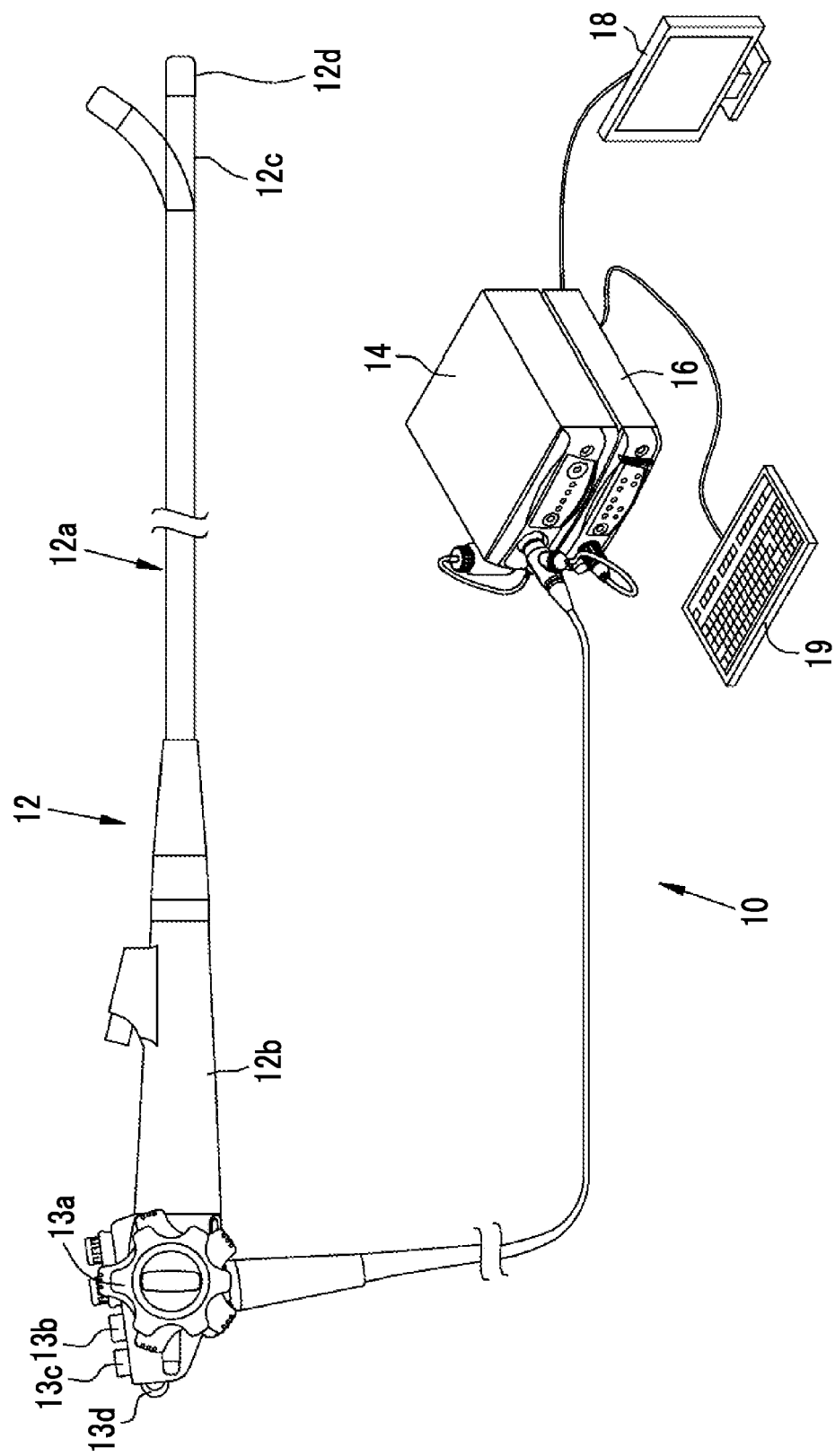
FIG. 1 is an external view of an endoscope system.

As illustrated in FIG. 1, an endoscope system 10 has an endoscope 12, a light source device 14, a processor device 16, a monitor 18 (display unit), and a console 19. The endoscope 12 is optically connected to the light source device 14, and is electrically connected to the processor device 16. The endoscope 12 has an insertion part 12a to be inserted into a subject, an operating part 12b provided at a proximal end portion of the insertion part 12a, and a bending part 12c and a distal end part 12d provided on a distal end side of the insertion part 12a. By operating an angle knob 13a of the operating part 12b, the bending part 12c makes a bending motion. The distal end part 12d is directed in a desired direction by this bending motion.

Additionally, the operating part 12b is provided with a still image acquisition unit 13b used for operating the acquisition of still images, a mode switching unit 13c used for operating the switching of observation modes, and a zooming operating unit 13d used for operating the change of a zoom magnification factor, in addition to the angle knob 13a. In the still image acquisition unit 13b, a freeze operation of displaying a still image of an observation target on the monitor 18, and a release operation of saving the still image in a storage are possible.

The endoscope system 10 has a normal mode, a special mode, and an index value display mode as the observation modes. In a case where an observation mode is the normal mode, normal light obtained by combining a plurality of colors of light components together in a quantity-of-light ratio Lc for normal mode is emitted, and a normal image is displayed on a monitor 18 on the basis of image signals obtained by imaging the observation target under illumination with this normal light. Additionally, in a case where an observation mode is the special mode, special light obtained by combining a plurality of colors of light components together in a quantity-of-light ratio Ls for special mode is emitted, and a special image is displayed on the monitor 18 on the basis of image signals obtained by imaging the observation target under illumination with this special light.

Additionally, in a case where an observation mode is the index value display mode, the special light is emitted, and index values, which are obtained by indexing shape features and the like of a vascular pattern on the basis of image signals obtained by imaging the observation target under illumination with special light, are calculated. In addition, an index value image obtained by imaging the index values is displayed on the monitor 18.

The processor device 16 is electrically connected to the monitor 18 and the console 19. The monitor 18 outputs and displays an image of the observation target, information accompanying the image, and the like. The console 19 functions as a user interface that receives input operations, such as designation or the like of a region of interest (ROI) and function setting. Hardware structures of the respective units within the processor device 16 are various processors as shown below. The various processors include a central processing unit (CPU) that is a general-purpose processor that executes software (programs) to function as various processing units, a programmable logic device (PLD) that is a processor capable of changing a circuit configuration after manufacture, such as a field programmable gate array (FPGA), and an exclusive electric circuit that is a processor having a circuit configuration exclusively designed to execute a specific process, such as an application specific integrated circuit (ASIC). In addition, the same applies the respective units inside the endoscope 12 and the light source device 14.

Figure 2:
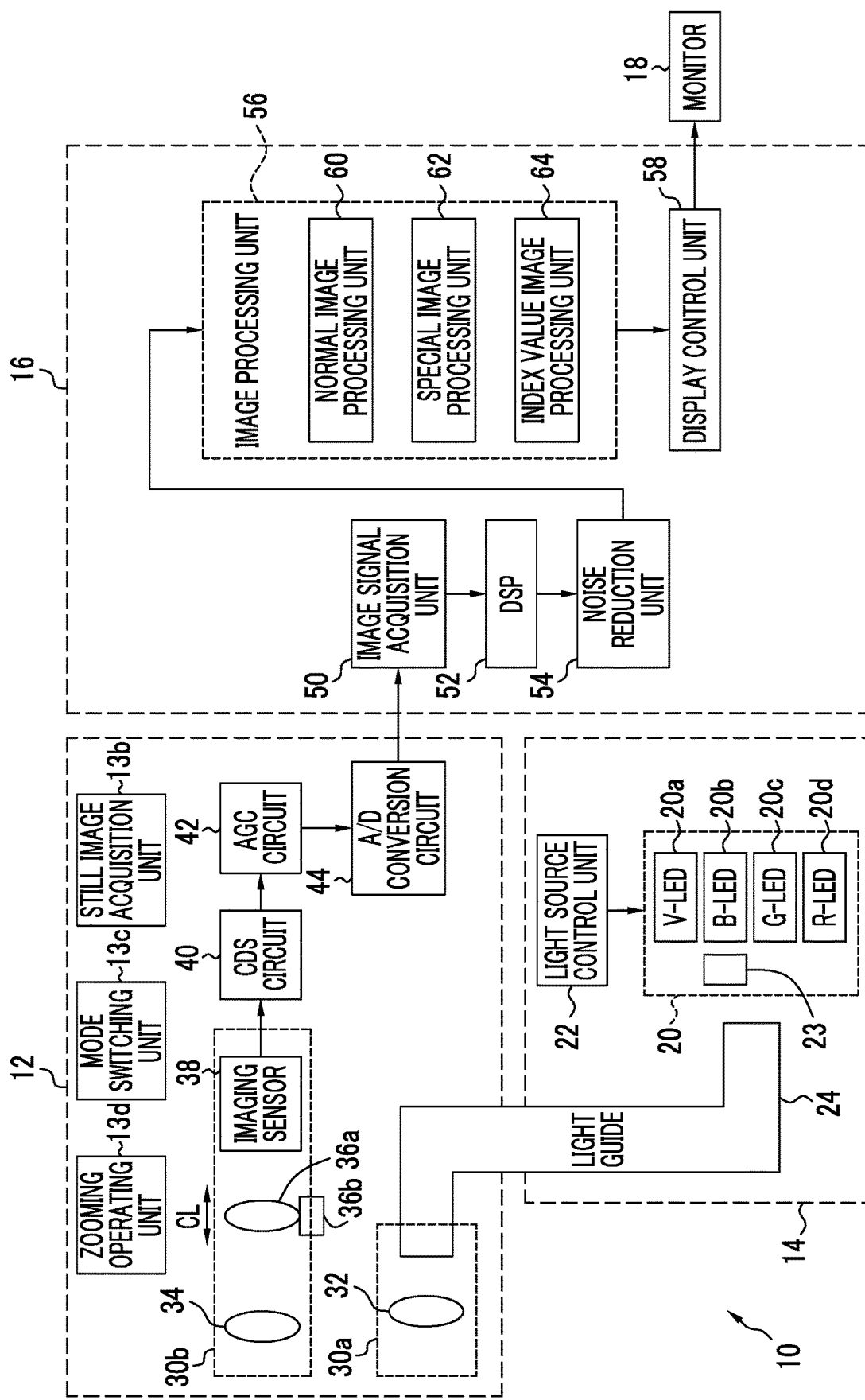
FIG. 2 is a block diagram illustrating functions of an endoscope system of a first embodiment.

As illustrated in FIG. 2, the light source device 14 comprises a light source 20 that emits the illumination light to be used for illumination of the observation target, and a light source control unit 22 that controls the light source 20. The light source 20 is semiconductor light sources, such as a plurality of colors of light emitting diodes (LEDs). The light source control unit 22 controls the quantity of light emission of the illumination light by ON/OFF of the LEDs and the adjustment of the driving currents or driving voltages of the LEDs. Additionally, the light source control unit 22 controls the wavelength range of the illumination light, by changing the optical filters or the like.

Figure 3:
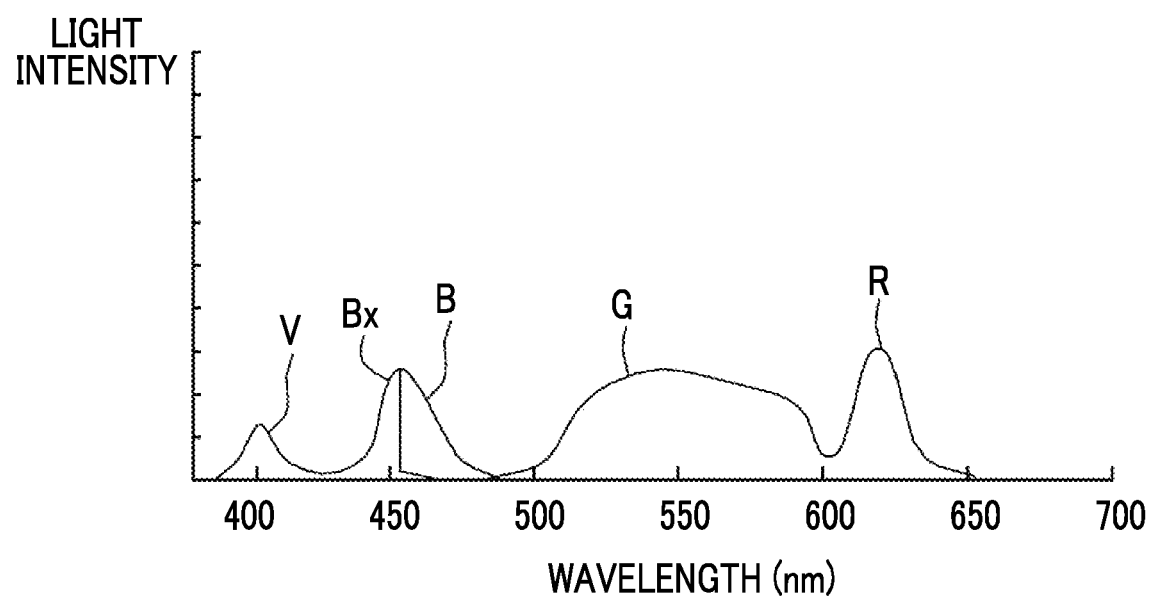
FIG. 3 is a graph illustrating a spectroscopic spectrum of violet light V, blue light B, blue light Bx, green light G, and red light R.

In the first embodiment, the light source 20 has four color LEDs of a violet light emitting diode (V-LED) 20a, a blue light emitting diode (B-LED) 20b, a green light emitting diode (G-LED) 20c, a red light emitting diode (R-LED) 20d, and a wavelength cutoff filter 23. As illustrated in FIG. 3, the V-LED 20a emits violet light V having a wavelength range of 380 nm to 420 nm.

The B-LED 20b emits blue light B having a wavelength range of 420 nm to 500 nm. The blue light B emitted from the B-LED 23b is cut by the wavelength cutoff filter 23 on at least a longer wavelength side than the peak wavelength 450 nm. Accordingly, the blue light Bx after being transmitted through the wavelength cutoff filter 23 has a wavelength range of 420 to 460 nm. In this way, the reason why light in a wavelength range on the longer wavelength side than 460 nm is cut is that the light in the wavelength range on the longer wavelength side than 460 nm is a factor in which the blood vessel contrast of blood vessels that is the observation target is lowered. In addition, the wavelength cutoff filter 23 may reduce the light in the wavelength range on the longer wavelength side than 460 nm instead of cutting the light in the wavelength range on the longer wavelength side than 460 nm.

The G-LED 20c emits green light G having a wavelength range of 480 nm to 600 nm. The R-LED 20d emits red light R having a wavelength range of 600 nm to 650 nm. In addition, center wavelengths and peak wavelengths of the respective light emitted from the LEDs 20a to 20d may be the same as each other or may be different from each other.

The light source control unit 22 independently controls ON/OFF of the respective LEDs 20a to 20d, the quantity of light emission at the time of ON, and the like, thereby adjusting the light emission timing of illumination light, a light emission period, the quantity of light, and a spectroscopic spectrum. The control of ON and OFF in the light source control unit 22 varies in the respective observation modes. In addition, the reference brightness is capable of being set by a brightness setting unit, the console 19, or the like of the light source device 14.

Figure 4:
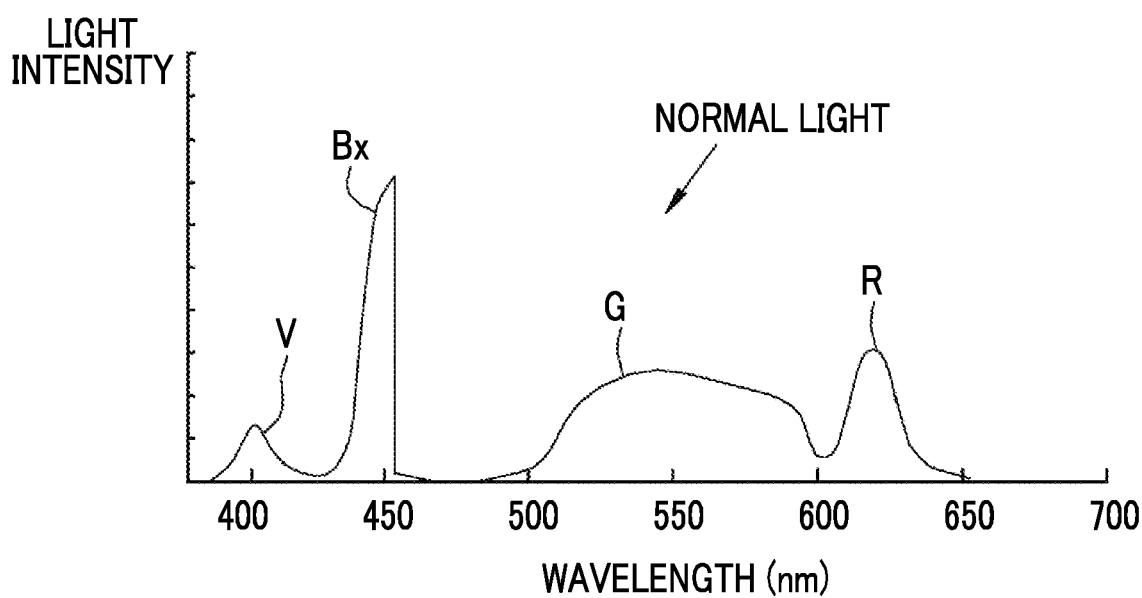
FIG. 4 is a graph illustrating a spectroscopic spectrum of normal light of the first embodiment.

In the case of the normal mode, the light source control unit 22 turns on the V-LED 20a, the B-LED 20b, the G-LED 20c, and the R-LED 20d altogether. In that case, as illustrated in FIG. 4, the quantity-of-light ratio Lc between the violet light V, the blue light B, the green light G, and the red light R is set such that the quantity of light emission of the blue light Bx becomes larger than the quantity of light emission of any of the violet light V, the green light G, and the red light R. Accordingly, in the normal mode, multicolor light for normal mode including the violet light V, the blue light Bx, the green light G, and the red light R is emitted as the normal light from the light source device 14. Since the normal light has an intensity equal to or more than a given level from a blue range to a red range, the normal light is substantially white.

Figure 5:
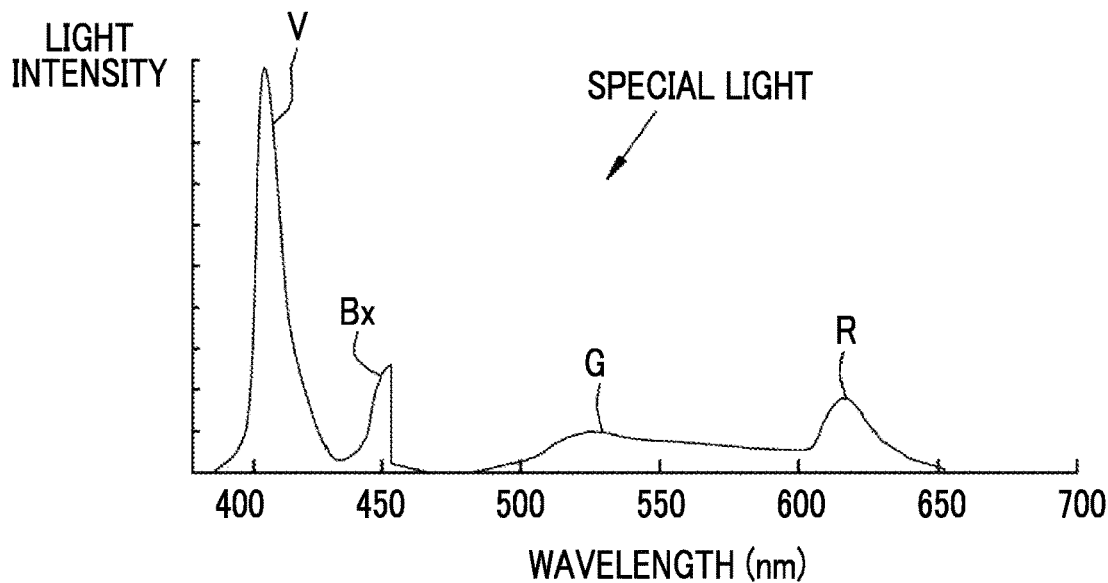
FIG. 5 is a graph illustrating a spectroscopic spectrum of special light of the first embodiment.

Even in the case of the special mode or the index value display mode, the light source control unit 22 turns on the V-LED 20a, the B-LED 20b, the G-LED 20c, and the R-LED 20d altogether. In that case, as illustrated in FIG. 5, the quantity-of-light ratio Ls between the violet light V, the blue light B, the green light G, and the red light R is set such that the quantity of light emission of the violet light V becomes larger than the quantity of light emission of any of the blue light Bx, the green light G, and the red light R and such that the green light G and the red light R become smaller than the violet light V and the blue light Bx. Accordingly, in the special mode or the index value display mode, multicolor light for special mode or index value display mode including the violet light V, the blue light Bx, the green light G, and the red light R is emitted as the special light from the light source device 14. Since the quantity of light emission of the violet light V is large, the special light is bluish light.

As illustrated in FIG. 2, the illumination light emitted from the light source 20 enters a light guide 24 inserted into the insertion part 12a via a light path coupling part (not illustrated) formed with a mirror, a lens, or the like. The light guide 24 is built in the endoscope 12 and a universal cord, and propagates the illumination light up to the distal end part 12d of the endoscope 12. The universal cord is a cord that connects the endoscope 12, and the light source device 14 and the processor device 16 together. In addition, multimode fiber can be used as the light guide 24. As an example, a fine-diameter fiber cable of which the core diameter is 105 μm, the clad diameter is 125 μm, and a diameter including a protective layer used as an outer cover is ϕ0.3 mm to ϕ0.5 mm can be used for the light guide 24.

The distal end part 12d of the endoscope 12 is provided with an illumination optical system 30a and an imaging optical system 30b. The illumination optical system 30a has an illumination lens 32. The observation target is illuminated with the illumination light propagated through the light guide 24 via the illumination lens 32. The imaging optical system 30b has an objective lens 34, a magnifying optical system 36, and an imaging sensor 38. Various kinds of light beams, such as reflected light from the observation target, scattered light, and fluorescence, enters the imaging sensor 38 via the objective lens 34 and the magnifying optical system 36. Accordingly, the image of the observation target is formed on the imaging sensor 38.

The magnifying optical system 36 comprises a zoom lens 36a that magnifies the observation target, and a lens drive unit 36b that moves the zoom lens 36a in an optical axis direction CL. The zoom lens 36a magnifies or reduces the observation target of which the image is formed on the imaging sensor 38 by freely moving between a telephoto end and a wide end in accordance with a zoom control performed by the lens drive unit 36b.

The imaging sensor 38 is a color imaging sensor that images the observation target irradiated with the illumination light. Each pixel of the imaging sensor 38 is provided with any one of a red (R) color filter, a green (G) color filter, or a blue (B) color filter. The imaging sensor 38 receives blue light with the B pixel provided with the B color filter from violet, receives green light with a G pixel provided with the G color filter, and receives red light with an R pixel provided with the R color filter. Image signals of respective RGB colors are output from the respective color pixels. The imaging sensor 38 transmits the output image signals to a CDS circuit 40.

In the normal mode, the imaging sensor 38 images the observation target illuminated with the normal light, thereby outputting a Bc image signal from the B pixel, outputting a Gc image signal from the G pixel, and outputting an Rc image signal from the R pixel. Additionally, in the special mode or the index value display mode, the imaging sensor 38 images the observation target illuminated with the special light, thereby outputting a Bs image signal from the B pixel, outputting a Gs image signal from the G pixel, and outputting an Rs image signal from the R pixel.

As the imaging sensor 38, a charge coupled device (CCD) imaging sensor, a complementary metal-oxide semiconductor (CMOS) imaging sensor, or the like is available. Additionally, instead of the imaging sensor 38 provided with the color filters in the primary colors of RGB, a complementary color imaging sensor comprising complementary color filters in C (cyan), M (magenta), Y (yellow), and G (green) may be used. In a case where the complementary color imaging sensor is used, image signals of four colors of CMYG are output. For this reason, the same respective RGB image signals as those in the imaging sensor 38 can be obtained by converting the image signals of four colors of CMYG into image signals of three colors of RGB through color conversion between complementary colors and the primary colors. Additionally, instead of the imaging sensor 38, a monochrome sensor that is not provided with the color filters may be used.

The CDS circuit 40 performs correlated double sampling (CDS) on analog image signals received from the imaging sensor 38. The image signals that have passed through the CDS circuit 40 are input to the AGC circuit 42. The AGC circuit 42 performs an automatic gain control (AGC) on the input image signals. An analog to digital (A/D) conversion circuit 44 converts an analog image signal passed through the AGC circuit 42 into a digital image signal. The digital image signal subjected to A/D conversion is input to the processor device 16 through the A/D conversion circuit 44.

The processor device 16 comprises an image signal acquisition unit 50, a digital signal processor (DSP) 52, a noise reduction unit 54, an image processing unit 56, and a display control unit 58.

The image signal acquisition unit 50 (equivalent to the "image acquisition unit" of the invention) acquires digital image signals corresponding to the observation modes from the endoscope 12. In the case of the normal mode, the Bc image signal, the Gc image signal, and the Rc image signal are acquired. In the case of the special mode or the index value display mode, the Bs image signal, the Gs image signal, and the Rs image signal are acquired.

The DSP 52 performs various kinds of signal processes, such as a defect correction process, an offset process, a DSP gain correction process, a linear matrix process, a gamma conversion process, a demosaicing process, and the like, on the image signals acquired by the image signal acquisition unit 50. In the defect correction process, a signal of a defective pixel of the imaging sensor 38 is corrected. In the offset process, a dark current component is removed from the image signals subjected to the defect correction process, and an accurate zero level is set. In the DSP gain correction process, a signal level is adjusted by multiplying the image signals subjected to the offset process by a specific DSP gain.

The linear matrix process enhances color reproducibility on the image signals subjected to the DSP gain correction process. In the gamma conversion process, brightness and saturation of image signals subjected to the linear matrix process are adjusted. By performing the demosaicing process (also referred to as an equalization process or a synchronization process) on the image signals subjected to the gamma conversion process, a signal of a color that runs short in each pixel is generated by interpolation. By means of this demosaicing process, all pixels have signals of respective RGB colors. The noise reduction unit 54 performs a noise reducing process using, for example, a moving average method, a median filter method, or the like on the image signals subjected to the demosaicing process or the like by the DSP 52, and reduces noise. The image signals after the noise reduction are input to the image processing unit 56.

The image processing unit 56 comprises a normal image processing unit 60, a special image processing unit 62, and an index value image processing unit 64. The normal image processing unit 60 operates in a case where the normal mode is set, and performs a color conversion process, a color enhancement process, and a structure enhancement process on the received Bc image signal, Gc image signal, and Rc image signal. In the color conversion process, a color conversion process is performed on the RGB image signals by a 3×3 matrix process, a gradation transformation process, a three-dimensional look-up table (LUT) process, and the like.

The color enhancement process is performed on the RGB image signals subjected to the color conversion process. The structure enhancement process is the process of enhancing the structure of the observation target, and is performed on the RGB image signals after the color enhancement process. The normal image is obtained by performing the various kinds of image processes as described above. Since the normal image is an image obtained on the basis of the normal light in which the violet light V, the blue light Bx, the green light G, and the red light R are emitted in a well-balanced manner, the normal image is a natural-tone image. The normal image is input to the display control unit 58.

The special image processing unit 62 operates in a case where the special mode is set. In the special image processing unit 62, the color conversion process, the color enhancement process, and the structure enhancement process is performed on the received Bs image signal, Gs image signal, and Rs image signal. The processing contents of the color conversion process, the color enhancement process, and the structure enhancement process are the same as those of the normal image processing unit 60. The special image is obtained by performing the various kinds of image processes as described above. Since the special image is an image obtained on the basis of special light in which the violet light V with a high absorption coefficient of hemoglobin of blood vessels has a larger quantity of light emission than the blue light Bx, the green light G, and the red light R in the other colors, the resolution of a blood vessel structure or a glandular structure is higher than that of the other structures. The special image is input to the display control unit 58.

The index value image processing unit 64 operates in a case where the index value display mode is set. The index value image processing unit 64 calculates index values obtained by indexing properties of various structures of the observation target including the blood vessel structure or the glandular structure on the basis of the received Bs image signal, Gs image signal, and Rs image signal. The index value image processing unit 64 can calculate a plurality of index values and calculates the index value according to the processing order for the index value calculation process which is preset on the basis of medical knowledge for the specific lesion. In addition, on the basis of the calculated index value, the index value image processing unit 64 determines a state of the mucous membrane in the specific lesion.

Furthermore, the index value image processing unit 64 generates an index value image on the basis of a calculation result of the index value, and in a case where the determination result of the state of the mucous membrane is obtained, the index value image processing unit 64 generates the index value image on which the determination result is superimposed and displayed. The index value image is input to the display control unit 58. The details of the index value image processing unit 64 will be described below.

The display control unit 58 performs a display control for displaying an image on the monitor 18 from the image processing unit 56. In a case where the normal mode is set, the display control unit 58 performs the control of displaying the normal image on the monitor 18. In a case where the special mode is set, the display control unit 58 performs the control of displaying the special image on the monitor 18. In a case where the index value display mode is set, the display control unit 58 performs the control of displaying the index value image on the monitor 18.

Figure 6:
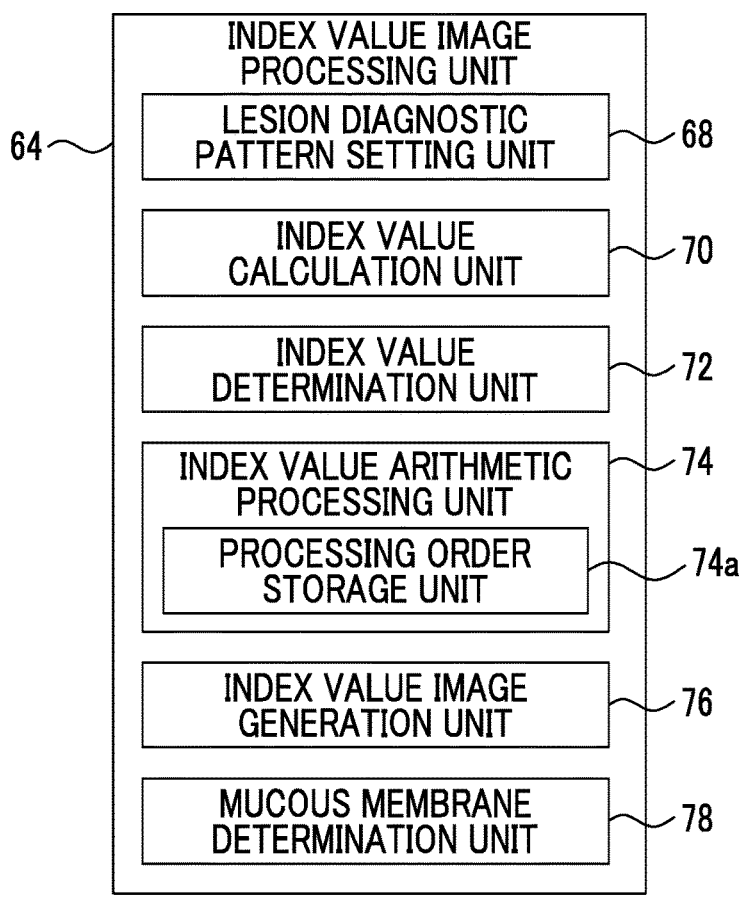
FIG. 6 is a block diagram illustrating functions of an index value image processing unit.

As illustrated in FIG. 6, the index value image processing unit 64 comprises a lesion diagnostic pattern setting unit 68, an index value calculation unit 70, an index value determination unit 72, an index value arithmetic processing unit 74, an index value image generation unit 76, and a mucous membrane determination unit 78. The lesion diagnostic pattern setting unit 68 sets a lesion diagnostic pattern to be used for determination of a type or stage of a specific lesion such as esophageal cancer or colorectal cancer on the basis of input information received from the console 19 or the like. The index value arithmetic processing unit 74 controls the index value calculation unit 70 and the index value determination unit 72 according to the lesion diagnostic pattern set by the lesion diagnostic pattern setting unit 68.

Figure 7:
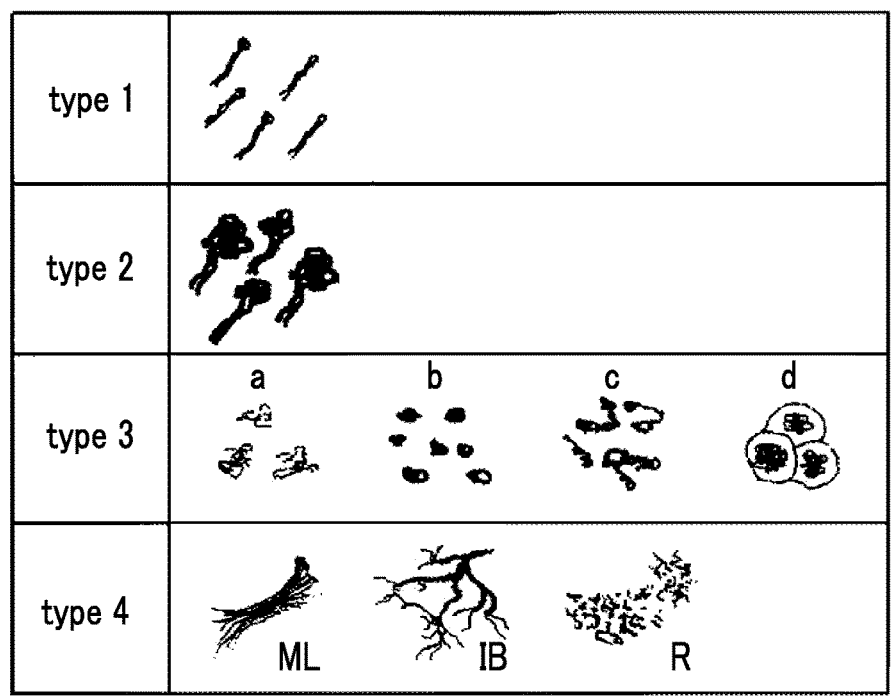
FIG. 7 is a table showing diagnostic patterns for esophageal cancer.

The lesion diagnostic pattern obtained by calculating and determining the index value in the present embodiment is determined on the basis of already established medical knowledge for a specific lesion. As examples of lesion diagnostic patterns for esophageal cancer (hereinafter, referred to as a "diagnostic pattern for esophageal cancer"), there is the microvascular pattern classification for esophageal cancer illustrated in FIG. 7 (refer to "Magnifying Endoscopy with FICE for the Screening and Differential Diagnosis of Small Squamous Cell Carcinomas of the Esophagus, Stomach and Intestine, 2009; 44: 1675-1687").

In the diagnostic pattern for esophageal cancer, type 1 is a vascular pattern in which thin and linear blood vessels are observed in papillae. type 2 is a vascular pattern in which blood vessels are extended, branched and enlarged, and have an increase in density but the structure is preserved, and an arrangement of the blood vessels is relatively regular and maintained. type 3a is a vascular pattern of broken filamentous. type 3b is a vascular pattern of crushed vessels with red spots. type 3c is a vascular pattern in which the blood vessels in type 3b are elongated and bound together. type 3d is a salmon roe-like vascular pattern in which spiral blood vessels are seen in papillary protrusions. type 4ML is a multi-layered vascular pattern. type 4IB is an irregularly branched vascular pattern. type 4R is a reticular vascular pattern.

In the diagnostic pattern for esophageal cancer, an invasion depth of esophageal cancer successively increases from type 1 toward type 4. In addition, in the diagnostic pattern for esophageal cancer, type 4 may further include subclasses of S (0.5 mm or less), M (more than 0.5 mm and 3 mm or less), and L (more than 3 mm) in terms of the avascular area (AVA) size.

As examples of lesion diagnostic patterns for colorectal cancer, there are pit pattern classification (magnifying classification of pit-like structures) in Hiroshima University (hereinafter, referred to as "a first diagnostic pattern for colorectal cancer"), Sano's vascular pattern (capillary pattern; CP) classification (hereinafter, referred to as "a second diagnostic pattern for colorectal cancer"), and vascular (microvessel construction) pattern classification (magnifying observation classification) considering the pit pattern in Jikei University School of Medicine (hereinafter, referred to as "a third diagnostic pattern for colorectal cancer").

Figure 8:
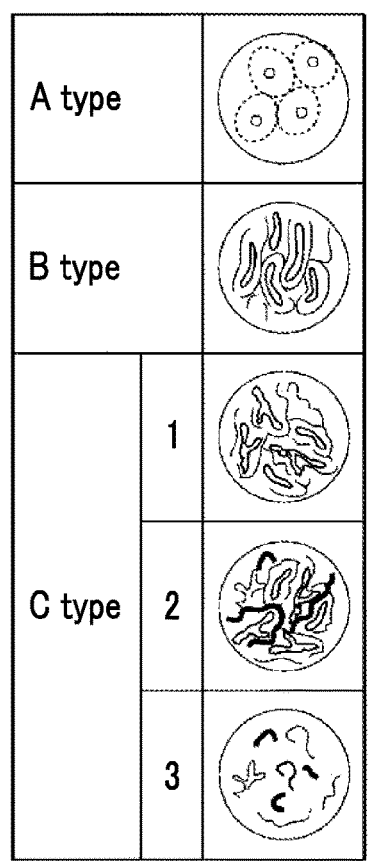
FIG. 8 is a table showing a first diagnostic pattern for colorectal cancer.

The first diagnostic pattern for colorectal cancer is the classification by the pit patterns as illustrated in FIG. 8. In the first diagnostic pattern for colorectal cancer, A type is a pit pattern having a normal color to brown color and no microvessel is visible. B type is a pit pattern in which a well-ordered clear pit-like structure is indirectly observed and which has a reticular microvessel architecture. C type 1 is a pit pattern indirectly having an irregular pit-like structure and blood vessels have a reticular architecture with relatively uniform thickness and distribution. C type 2 is a pit pattern indirectly having a highly irregular pit-like structure and blood vessels have a reticular architecture with non-uniform thickness and distribution. C type 3 is a pit pattern in which an irregular pit-like structure is unclear and unobservable, blood vessels are irregular and have non-uniform thickness and distribution, an avascular area appears, and scattered microvessel fragments are observed. In the above first diagnostic pattern for colorectal cancer, the invasion depth of colorectal cancer successively increases from A type toward C type. In addition, in C type, the invasion depth of colorectal cancer successively increases from 1 toward 3.

Figure 9:
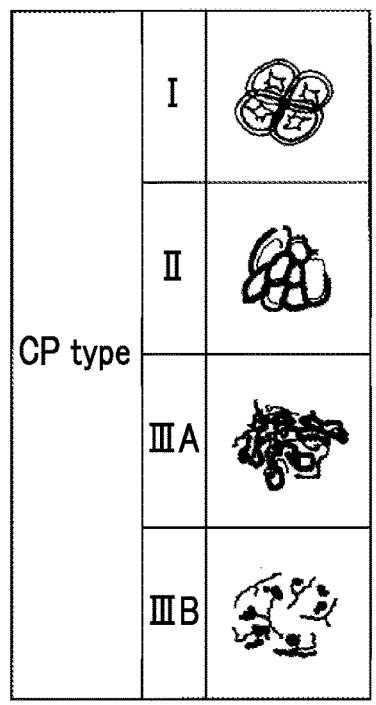
FIG. 9 is a table showing a second diagnostic pattern for colorectal cancer.

The second diagnostic pattern for colorectal cancer is a vascular pattern classification as illustrated in FIG. 9. In the vascular pattern classification, CP type I is a vascular pattern in which the microvessel can not be identified. CP type II is a vascular pattern in which blood vessels surrounding the periphery of each glandular duct can be observed and the blood vessel diameters are uniform. CP type IIIA is a vascular pattern in which blood vessels are not well ordered and irregular blood vessels are clearly seen. CP type IIIB is a vascular pattern in which blood vessels are not well ordered and irregular blood vessels are unclearly seen. In the second diagnostic pattern for colorectal cancer, the invasion depth of colorectal cancer successively increases from CP type I toward CP type III, and in CP type III, the invasion depth is larger in B than in A.

Figure 10:
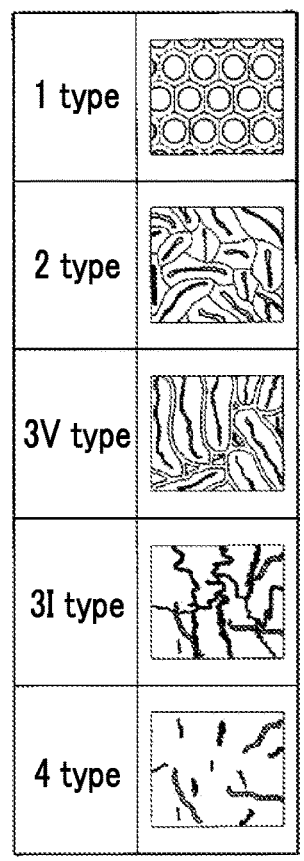
FIG. 10 is a table showing a third diagnostic pattern for colorectal cancer.

The third diagnostic pattern for colorectal cancer is a vascular pattern classification as illustrated in FIG. 10. In the third diagnostic pattern for colorectal cancer, 1 type is a vascular pattern in which traveling of blood vessels is not seen. 2 type is a vascular pattern in which a slight increase in the blood vessel diameter is seen. 3 type is a vascular pattern in which an increase in the blood vessel diameter is clearly seen, and 3V type is a vascular pattern that exhibits a cilia-like structure and in which the enlarged blood vessels regularly travel along the glandular duct interstitium. 3I type is a vascular pattern in which the enlarged blood vessels irregularly travel. 4 type is a vascular pattern in which blood vessels are sparsely distributed and no traveling of the blood vessels can be seen. In the third diagnostic pattern for colorectal cancer, the invasion depth of colorectal cancer successively increases from 1 type toward 4 type, and in 3 type, the invasion depth is larger in I type than in V type.

The index value calculation unit 70 performs the index value calculation process of calculating index values obtained by indexing the property of various structures of the observation target including the blood vessel structure or the glandular structure on the basis of the Bs image signal, Gs image signal, and Rs image signal. In a case where an index value calculation instruction is given by the index value arithmetic processing unit 74, the index value calculation unit 70 performs the index value calculation process on the basis of the index value calculation instruction.

For example, in a case where the index value calculation process performed by the index value arithmetic processing unit 74 is a process of calculating a blood vessel density, a blood vessel extraction process of extracting blood vessels is firstly performed. As the blood vessel extraction process, for example, an image in which blood vessels having different depths are extracted can be obtained by processing a difference between the Bs image signal and the Gs image signal. Then, by calculating a ratio occupied by blood vessels in the blood vessel extraction image, the blood vessel density is obtained.

In a case where an index value determination instruction is given by the index value arithmetic processing unit 74, the index value determination unit 72 performs the index value determination process of determining whether or not a reference of the index value corresponding to the lesion diagnostic pattern is satisfied for the index value calculated by the index value calculation unit 70. For example, it is preferable that the reference of the index value at the time of determining which type 1 or type 2 is corresponding to the diagnostic pattern for esophageal cancer is a reference whether or not the thickness of the blood vessel is smaller than a specific thickness thereof.

The index value arithmetic processing unit 74 controls the index value calculation unit 70 or the index value determination unit 72 according to the processing order for the index value calculation process or the index value determination process which is predetermined on the basis of medical knowledge for a specific lesion. The index value arithmetic processing unit 74 performs control by referring to a processing order storage unit 74a that stores the lesion diagnostic pattern in association with the processing order for the index value calculation process or the index value determination process. As illustrated in FIG. 11, a plurality of processing orders, which include a processing order for esophageal cancer determined on the basis of the diagnostic pattern for esophageal cancer, a first processing order for colorectal cancer determined on the basis of the first diagnostic pattern for colorectal cancer, a second processing order for colorectal cancer determined on the basis of the second diagnostic pattern for colorectal cancer, and a third processing order for colorectal cancer determined on the basis of the third diagnostic pattern for colorectal cancer, are stored in the processing order storage unit 74a in association with a specific lesion diagnostic pattern.

A plurality of processing routes corresponding to the result of the index value determination process are set in the processing order. As a method of setting the processing route, for example, it is preferable to set the processing route in which the type of the index value to be subsequently calculated can be changed according to the result of the index value determination process. Furthermore, it is preferable to set the processing route in which the number of index values to be subsequently calculated can be increased or decreased according to the result of the index value determination process.

Here, the control performed by the index value arithmetic processing unit 74 on the basis of the processing order for esophageal cancer will be described with reference to FIG. 12. First, in a case where the diagnostic pattern for esophageal cancer is set by the lesion diagnostic pattern setting unit 68, the index value arithmetic processing unit 74 instructs the index value calculation unit 70 to perform an initial index value calculation process with reference to the processing order for esophageal cancer stored in the processing order storage unit 74a. The processing order storage unit 74a is formed of recording media such as a hard disk drive (HDD) or a solid state drive (SSD). In the initial index value calculation process, an initial index value that is common to many lesions and can roughly identify the possibility of lesion is calculated. The initial index value includes, for example, a difference in a mucous membrane color or a blood vessel density. The calculation of the initial index value may be performed for each frame illuminated with special light or may be performed at several frame intervals. Furthermore, the calculation may be performed at a time preset by a user according to the instruction input from the console 19 or the like, or may be performed only at a time of activating the index value display mode.

Next, the index value arithmetic processing unit 74 instructs the index value determination unit 72 to perform an initial index value determination process of determining whether or not the initial index value meets the reference for the initial index value. Thus, the index value determination unit 72 performs the initial index value determination process, and then determines that the state of the mucous membrane in the observation target is normal in a case where the initial index value satisfies the reference for the initial index value. For example, assuming that the initial index value represents a difference in a mucous membrane color or a blood vessel density, in a case where a region that has a color different from the normal mucous membrane color is less than a certain area or in a case where there is no region where the blood vessel density is a predetermined value or more, the index value determination unit 72 determines that the state of the mucous membrane in the observation target is normal. It is preferable that the result in the determination of normality is displayed in the index value image. In a case where the index value determination unit 72 determines that a state of a mucous membrane is normal, the index value display mode is ended and switched to the normal mode or the special mode, or the index value display mode may be continued until the index value determination unit 72 determines that a state of a mucous membrane is abnormal.

On the other hand, in a case where the initial index value does not satisfy the reference for the initial index value, the index value determination unit 72 determines that the state of the mucous membrane is abnormal. For example, assuming that the initial index value represents a difference in a mucous membrane color or a blood vessel density, in a case where a region that has a color different from the normal mucous membrane color is equal to or more than a certain area or in a case where there is a region where the blood vessel density is a predetermined value or more, the index value determination unit 72 determines that the state of the mucous membrane in the observation target is abnormal. In a case where the index value determination unit 72 determines that the state of the mucous membrane is abnormal, the index value arithmetic processing unit 74 instructs the index value calculation unit 70 to perform the first index value calculation process. In the first index value calculation process, it is preferable to calculate a first index value in the region where the state of the mucous membrane is determined to be abnormal. The region where the state of the mucous membrane is determined to be abnormal is, for example, a region that has a color different from the normal mucous membrane color or a region where blood vessel density is a predetermined value or more. Furthermore, it is preferable that the first index value is an index value suitable for distinguishing between linear type vascular patterns of type 1 and 2 and non-uniform vascular patterns of types 3 and 4. For example, it is preferable that the first index value is a blood vessel length.

Next, in a case where the first index value is calculated, the index value arithmetic processing unit 74 instructs the index value determination unit 72 to perform the first index value determination process. In the first index value determination process, a determination of whether or not the first index value satisfies the reference for the first index value corresponding to the diagnostic pattern for esophageal cancer is performed. Based on the reference for the first index value, it is determined that the first index value is included in at least one of a range of index values corresponding to a linear vascular pattern, a range of index values corresponding to a non-uniform vascular pattern, or a range of index values that are not included in any patterns.

Next, the first index value determination process is completed, and then the index value arithmetic processing unit 74 controls the index value calculation unit 70 so that the second index value calculation process is performed according to the result of the determination performed in the first index value determination process. In the second index value calculation process, the second index value is selected from the plurality of index values according to the result of the first index value determination process, and the selected second index value is calculated. Specifically, in a case where the result of the first index value determination process is a first determination result in which the first index value is a value determined to be included in the range of the index value corresponding to the linear vascular pattern, the second index value for the first determination result suitable for distinguishing between the thin vascular pattern of type 1 and the thick vascular pattern of type 2 is selected and calculated as the second index value calculation process. The second index value for the first determination result is preferably, for example, a thickness of the blood vessel.

On the other hand, in a case where the first index value is a value obtained from a second determination result determined to be included in the range of the index value corresponding to the non-uniform vascular pattern, the second index value for the second determination result suitable for distinguishing between a vascular pattern of type 3 and a vascular pattern of type 4 is selected and calculated as the second index value calculation process. As the second index value for the second determination result, it is preferable to use a meandering degree, a complexity, the number of branches, and the like of the blood vessel. In addition, since the vascular patterns of type 3 and type 4 have various shapes respectively, a pattern matching process based on templates of type 3 and type 4 may be performed instead of or in addition to the second index value calculation process. Furthermore, in a case where the first index value is a value obtained from a third determination result determined to be included in the range of the index value corresponding to the vascular patterns that are not included in the linear vascular pattern or the non-uniform vascular pattern, the index value arithmetic processing unit 74 performs a pattern matching process based on templates of type 1 to type 4.

In a case of performing the index value calculation process or the index value determination process, the index value arithmetic processing unit 74 determines whether all of the index values for mucous membrane determination, which are required to determine the state of the mucous membrane, are prepared or not. In addition, for each index value calculation process, the index value arithmetic processing unit 74 instructs the index value image generation unit 76 to generate the index value image on the basis of the calculated index value. The index value image generated by the index value image generation unit 76 is displayed on the monitor 18 by the display control unit 58.

Figure 13:
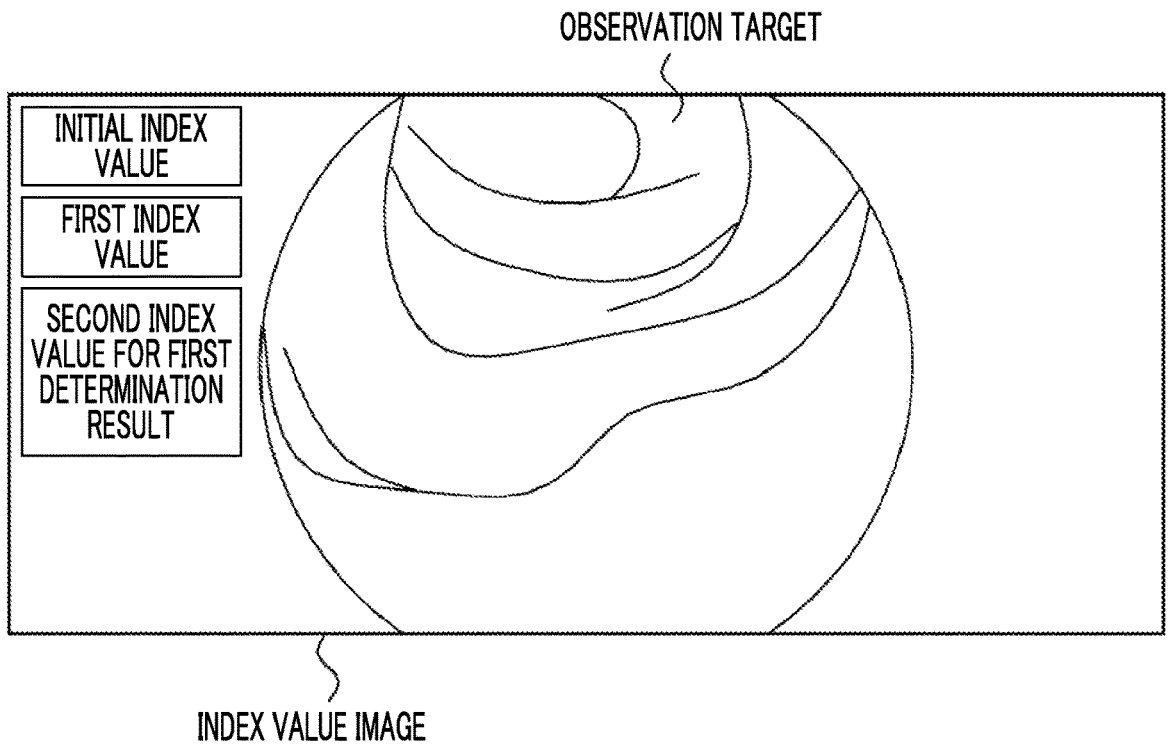
FIG. 13 is an image diagram illustrating an index value image on which index values are displayed.

The display control unit 58 performs a control so as to display the calculated index value on the index value image for each index value calculation process. For example, as illustrated in FIG. 13, in a case where a calculation of the second index value for the first determination result is completed, not only the second index value for the first determination result but also the initial index value and the first index value calculated so far are superimposed and displayed on the index value image together with the image of the observation target. Since only the index value required to determine the state of the mucous membrane that may become esophageal cancer is displayed on the monitor 18, a diagnosis of esophageal cancer can be made easier. In a case where the pattern matching process is performed, a vascular pattern obtained from the result of pattern matching processing may be displayed in the index value image. In addition, the display control unit 58 displays all of the index values calculated so far for each index value calculation process. However, only the most recent two or three index values may be displayed. Furthermore, once new index values are calculated, only the new index values may be displayed so that the index values calculated in the past are not displayed.

Figure 14:
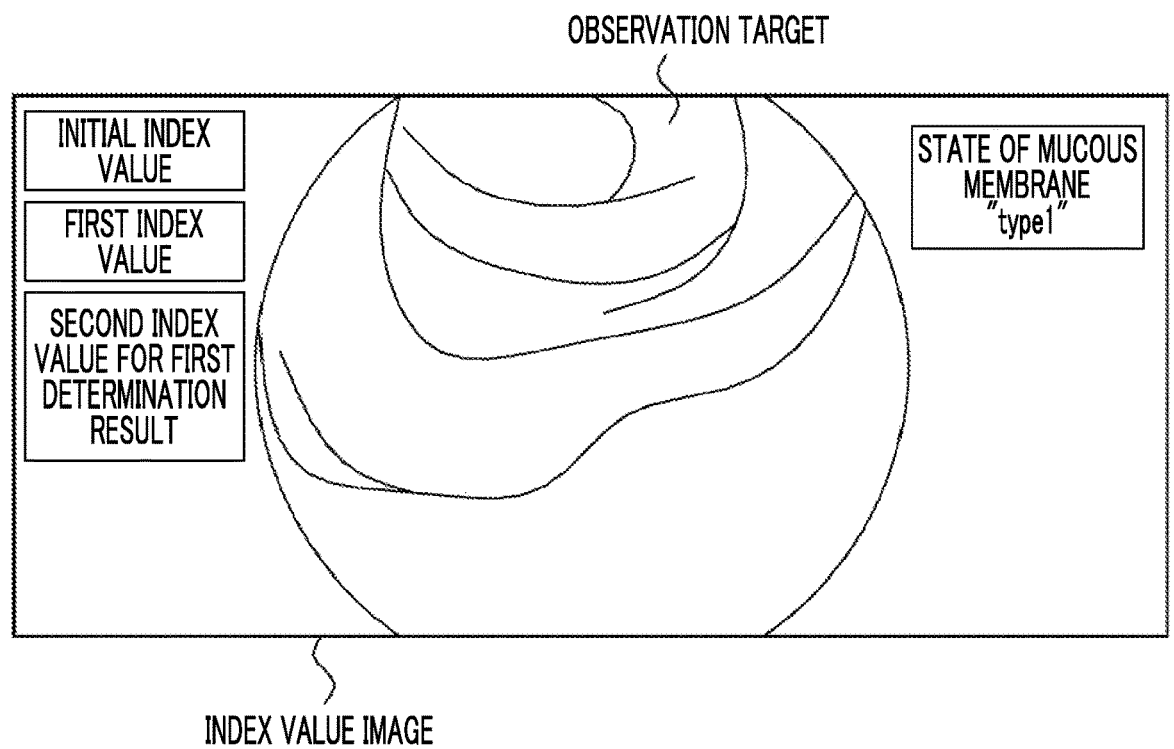
FIG. 14 is an image diagram illustrating an index value image on which the index values and a determination result of a mucous membrane are displayed.

The index value arithmetic processing unit 74 instructs the mucous membrane determination unit 78 to perform a mucous membrane determination process of determining the state of the mucous membrane in a stage of determining that all of the index values for mucous membrane determination are prepared. Examples of the state of the mucous membrane include a type of a lesion, a degree of progress of the lesion, a normal mucous membrane and the like. In a case where the calculation of the second index value for the first determination result is completed, the mucous membrane determination unit 78 performs the mucous membrane determination process of determining the state of the mucous membrane on the basis of the initial index value, the first index value, and the second index value for the first determination result. The mucous membrane determination unit 78 determines that the state of the mucous membrane is "type 1" in a case where the second index value for the first determination result is included in a range of the index value corresponding to the thin vascular pattern of type 1. On the other hand, the mucous membrane determination unit 78 determines that the state of the mucous membrane is "type 2" in a case where the second index value for the first determination result is included in a range of the index value corresponding to the thick vascular pattern of type 2. The determination result obtained by the mucous membrane determination unit 78 is displayed alone on the index value image or on the index value image together with the index value as illustrated in FIG. 14.

Figure 12:
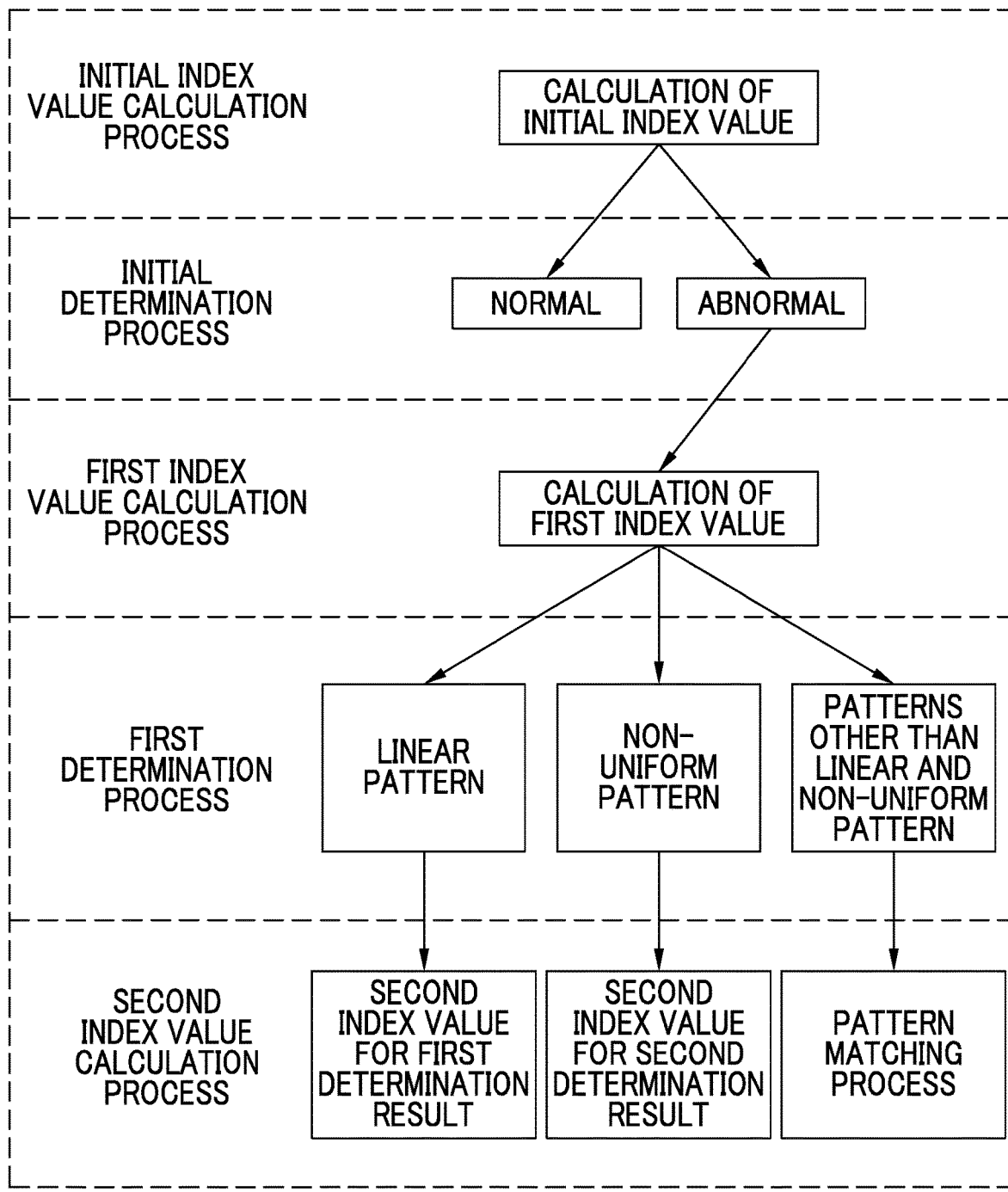
FIG. 12 is an explanatory view illustrating the processing order for esophageal cancer.

As described above, in the processing order for esophageal cancer, four first to fourth processing routes corresponding to the result of the index value determination process are set (refer to FIG. 12). That is, the first processing route is a route in which the initial index value calculation process is performed, the initial index value determination process is performed, and then the state of the mucous membrane is determined to be "normal". The second to fourth processing routes are the routes in which the initial index value calculation process is performed, the initial index value determination process is performed, the state of the mucous membrane is determined to be "abnormal", and thereafter a first index value calculation process is performed. The second processing route among these second to fourth processing routes is a route in which the first determination result is obtained from the first index value determination process, and thereafter the second index value for the first determination result is calculated. The third processing route is a route in which the second determination result is obtained from the first index value determination process, and thereafter the second index value for the second determination result is calculated. The fourth processing route is a route in which the third determination result is obtained from the first index value determination process, and thereafter the pattern matching process is performed.

Figure 15:
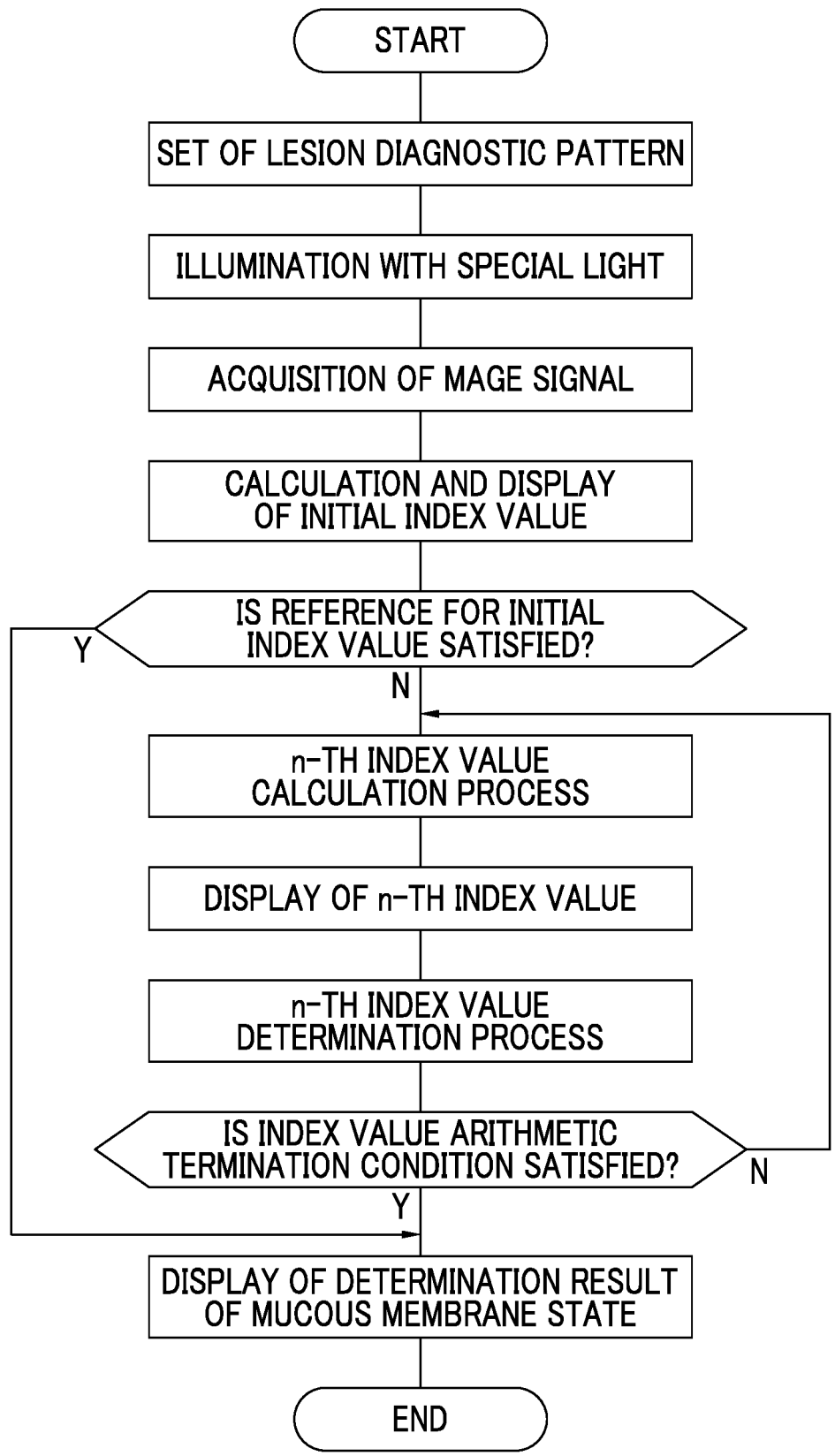
FIG. 15 is a flowchart illustrating a series of flow in an index value display mode.

Next, a series of flows in the index value display mode will be described using a flowchart illustrated in FIG. 15. First, in a case where the index value display mode is set by the mode switching unit 13c, a guidance prompting to set the lesion diagnostic pattern is displayed on the monitor 18. In accordance with the display, the lesion diagnostic pattern is input by the user using the console 19 or the like. In accordance with the input, the lesion diagnostic pattern setting unit 68 sets a lesion diagnostic pattern. In addition, the observation target is irradiated with special light. The imaging sensor 38 outputs the Bs image signal, the Gs image signal, and the Rs image signal by imaging the observation target illuminated with the special light.

In a case where the Bs image signal, the Gs image signal, and the Rs image signal are obtained, the index value arithmetic processing unit 74 selects the processing order corresponding to the lesion diagnostic pattern by referring to the processing order storage unit 74a, and controls the index value calculation unit 70 and the index value determination unit 72 according to the selected processing order. First, the index value arithmetic processing unit 74 instructs the index value calculation unit 70 to calculate an initial index value. The index value calculation unit 70 calculates the initial index value on the basis of the Bs image signal, the Gs image signal, and the Rs image signal. The calculated initial index value is displayed in the index value image on the monitor 18 according to the display control of the display control unit 58. Generating the index value image is performed by the index value image generation unit 76. In a case where the initial index value is calculated, the index value arithmetic processing unit 74 performs the initial index value determination process of determining whether or not the initial index value satisfies the reference for the initial index value.

As a result of the initial index value determination process, in a case where the index value is determined to be normal, the index value arithmetic processing unit 74 instructs the index value image generation unit 76 to generate the index value image. The index value arithmetic processing unit 74 generates the index value image on the basis of the Bs image signal, the Gs image signal, and the Rs image signal, and displays "normal" in the index value image.

On the other hand, as a result of the initial index value calculation process, in a case where the index value is determined to be abnormal, the index value arithmetic processing unit 74 instructs the index value calculation unit 70 or the index value determination unit 72 to perform the n-th (n is a natural number of 1 or more) index value calculation process or the n-th (n is a natural number of 1 or more) index value determination process. First, the index value calculation unit 70 performs the first index value calculation process to calculate the first index value. The calculated first index value is displayed in the index value image on the monitor 18 according to the display control of the display control unit 58. In a case where the first index value is calculated, the index value arithmetic processing unit 74 instructs the index value determination unit 72 to perform the first index value determination process of determining the first index value on the basis of the reference for the first index value. The index value determination unit 72 performs the first index value determination process and outputs a plurality of determination results including the first determination result and the second determination result.

Next, the index value arithmetic processing unit 74 selects the second index value according to the result of the first index value determination process among the plurality of index values, and instructs the index value calculation unit 70 to perform the second index value calculation process of calculating the selected second index value. The index value calculation unit 70 performs the second index value calculation process to calculate a plurality of second index values including the second index value for the first determination result and the second index value for the second determination result. The calculated second index value is displayed in the index value image on the monitor 18 together with the first index value calculated in advance according to the display control of the display control unit 58.

In a case where the second index value is calculated, as described above, the index value arithmetic processing unit 74 performs the index value calculation process or the index value determination process until an index value arithmetic termination condition is satisfied according to the processing order determined on the basis of the lesion diagnostic pattern. For example, in a case where the index value arithmetic termination condition is to perform the index value calculation process and the index value determination process for N times (N is a natural number of 2 or more), the index value calculation process or the index value determination process is repeated N times. In a case where the index value arithmetic termination condition is to calculate all of the index values for mucous membrane determination, the index value calculation process or the index value determination process is repeated until all of the calculations of the index values for the mucous membrane determination are completed.

In a case where the index value arithmetic termination condition is satisfied and the mucous membrane determination unit 78 determines the mucous membrane, the determination result of the mucous membrane is displayed in the index value image together with the index value calculated in advance. Alternatively, it is not limited to this, and only the mucous membrane determination result may be displayed, and the calculated index value may not be displayed.

Figure 16:
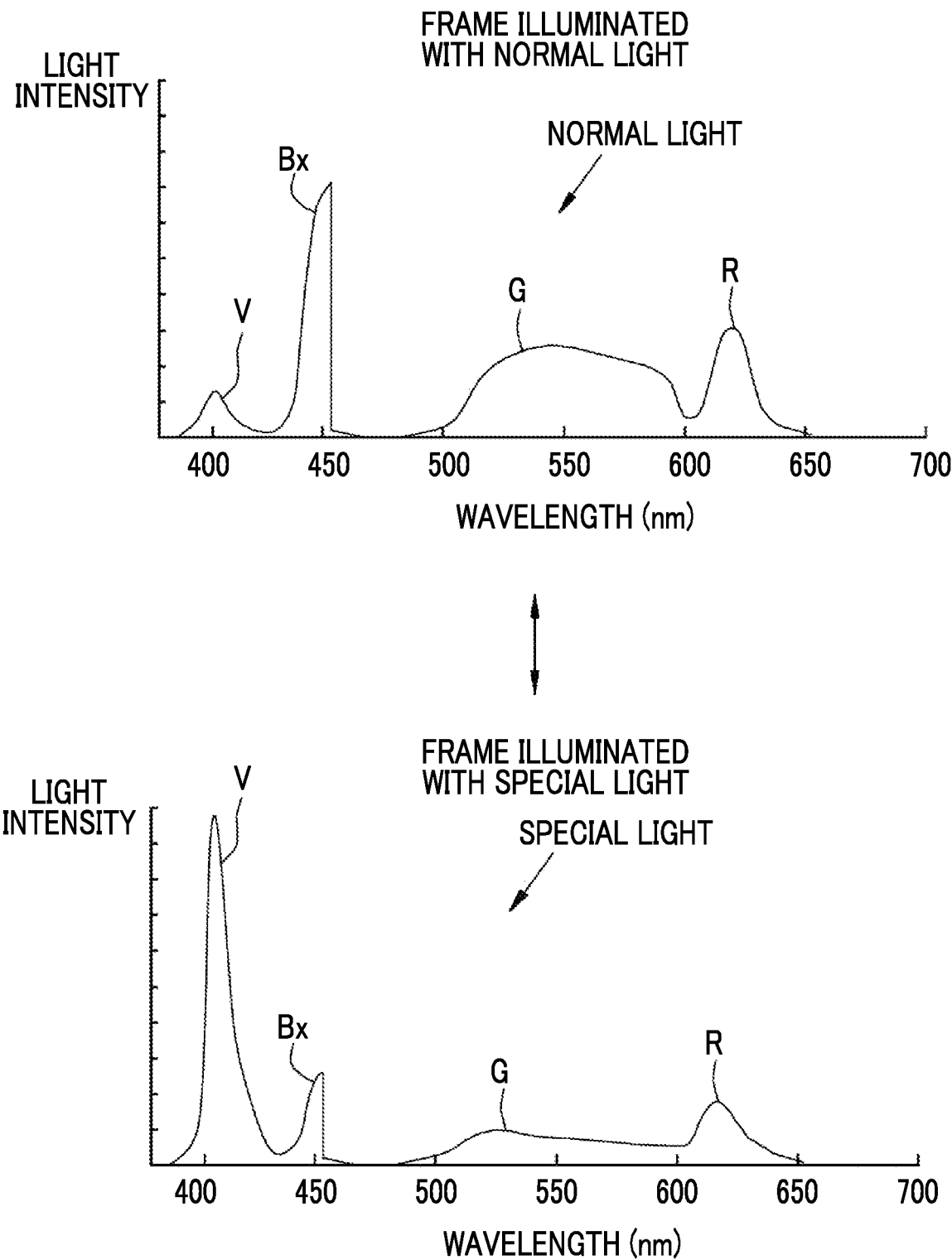
FIG. 16 is an explanatory diagram illustrating that frames are alternately illuminated with normal light and special light.

In the above embodiment, in the index value display mode, each frame is illuminated with special light to perform the calculation of the index value and the generation of the index value image. However, a plurality of multi-frames may be illuminated with a plurality of kinds of light beams respectively, and the index value image generation unit may generate a plurality of images including an image for index value calculation on the basis of a multi-frame image signal obtained by illuminating and imaging the multi-frames. For example, as illustrated in FIG. 16, frames different from each other are illuminated with normal light and special light respectively. Then, a normal image is generated on the basis of the normal light, and a calculation of the index value and a generation of the index value image are performed from the image for index value calculation obtained on the basis of the special light. In this case, it is preferable that the generated normal image and the index value image are displayed side by side on the monitor 18, or alternately displayed at a specific display timing.

In addition, in the above embodiment, the blood vessel density and the blood vessel thickness have been shown as specific examples of the index values. However, other index values may be used. As the index values of the blood vessels, for example, the number of pieces, the number of branches, a branch angle, a distance between branch points, the number of intersections, a change in thickness, intervals, depth with a mucous membrane as a reference, a height difference, inclination, contrast, color, a change in color, the degree of meandering, blood concentration, oxygen saturation, an artery proportion, a vein proportion, the concentration of an input coloring agent, a traveling pattern, blood flow rate, and the like, in terms of the blood vessels.

The number of blood vessels is the number of blood vessels extracted within the overall endoscopic image or the region of interest. The number of blood vessels is calculated, for example, using the number of branch points (the number of branches) of the extracted blood vessels, the number of intersection points (the number of intersections) with other blood vessels, or the like. The branch angle of blood vessels is an angle that two blood vessels form at a branch point. The distance between the branch points is a linear distance between an optional branch point and its adjacent branch point, and a length along a blood vessel from the optional branch point and its adjacent branch point.

The number of intersections of blood vessels is the number of intersection points where blood vessels with different depths under the mucous membrane intersect each other on the endoscopic image. More specifically, the number of intersections of blood vessels is the number of times with which blood vessels at a relatively shallow position under the mucous membrane intersect blood vessels at a relatively deep position.

The thickness (blood vessel diameter) of the blood vessel is a distance between boundary lines of the blood vessel and the mucous membrane. For example, the distance is calculated by counting the number of pixels along a lateral direction of the blood vessel passing through the blood vessel from an edge of the extracted blood vessel. Therefore, the thickness of the blood vessel is the number of pixels, and in a case where the imaging distance, zoom magnification and the like are known at a time of imaging an endoscopic image, it is possible to be converted into a length such as "µm" as necessary.

The change in the thickness of the blood vessels is blood vessel information on variations in the thickness of the blood vessel, and is also referred to as the degree of aperture inequality. The change in thickness of blood vessels is, for example, the change rate (also referred to as the degree of dilation) of the blood vessel diameter. The change rate of the blood vessel diameter is calculated from "Change rate (%) of blood vessel diameter=Minimum diameter/Maximum diameter×100", using the thickness (minimum diameter) of the thinnest portion of a blood vessel, and the thickness (maximum diameter) of a thickest portion of a blood vessel.

In addition, in a case where an endoscopic image obtained by imaging the observation target in the past inspection and an endoscopic image obtained by imaging the same observation target in subsequent new inspection, a time change in the thickness of the same blood vessel extracted from the endoscopic image obtained in the subsequent new inspection with respect to the thickness of the blood vessel extracted from the endoscopic image obtained in the past inspection may be used as the change in the thickness of the blood vessels.

Additionally, the percentage of a smaller-diameter part or the percentage of a larger-diameter part may be calculated as the change in the thickness of the blood vessels. The smaller-diameter part is a portion of which the thickness is equal to or smaller than a threshold value and the larger-diameter part is a portion of which the thickness is larger than the threshold value. The percentage of the smaller-diameter part is calculated from "Percentage (%) of smaller-diameter part=Length of smaller-diameter part/Length of blood vessel×100". Similarly, the percentage of the larger-diameter part is calculated from "Percentage (%) of larger-diameter part=Length of larger-diameter part/Length of blood vessel×100"

In a case where the thickness of the blood vessel changes, the complexity of a change in thickness of blood vessels (hereinafter, referred to as "the complexity of the thickness change") is blood vessel information indicating how complex the change is, and is blood vessel information that is calculated by combining a plurality of pieces of blood vessel information representing a change in the thickness of the blood vessel (that is, the change rate of the blood vessel diameter, the percentage of the smaller-diameter part, or the percentage of the larger-diameter part). The complexity of the thickness change can be obtained, for example, by the product of the change rate of the blood vessel diameter and the percentage of the smaller-diameter part.

The length of the blood vessel is the number of pixels counted along a longitudinal direction of the extracted blood vessel.

The interval of blood vessels is the number of pixels representing the mucous membrane between edges of extracted blood vessels. In a case where there is one extracted blood vessel, the interval of blood vessels does not have a value.

The depth of blood vessels is measured on the basis of the mucous membrane (more specifically, a surface of the mucous membrane). The depth of blood vessels with this mucous membrane as a reference can be calculated, for example, on the basis of the color of blood vessels. In the case of the special observation image, a blood vessel at a position near the surface of the mucous membrane is expressed in the magenta-based color and a blood vessel at a position distant from the surface of the mucous membrane and deep under the mucous membrane is expressed in the cyan-based color. Thus, the blood vessel information calculation unit 83 calculates the depth of the blood vessels with the mucous membrane as a reference for each pixel, on the basis of the balance between signals in respective colors of R, G, and B of pixels extracted as the blood vessels.

The height difference of blood vessels is the magnitude of a difference in depth of a blood vessel. For example, the height difference of one blood vessel to be observed is calculated from a difference between the depth (maximum depth) of the deepest location of this blood vessel, and the depth (minimum depth) of the shallowest location. The height difference is zero in a case where the depth is constant.

The inclination of blood vessels is the change rate of the depth of a blood vessel, and is calculated using the length of the blood vessel and the depth of the blood vessel. That is, the inclination of blood vessels is calculated from "Inclination of blood vessel=Depth of blood vessel/Length of blood vessel". In addition, a blood vessel may be divided into a plurality of sections, and the inclination of the blood vessel may be calculated in each section.

The area of the blood vessel is a value proportional to the number of pixels of a pixel extracted as a blood vessel. The area of the blood vessel is calculated within the region of interest, outside the region of interest, or the entire endoscopic image.

The contrast of the blood vessels is a relative contrast of the observation target with respect to the mucous membrane. The contrast of the blood vessels is calculated, for example, from "$Y_V/Y_M$" or "$(Y_V-Y_M)/(Y_V+Y_M)$", using the brightness $Y_V$ of blood vessels, and the brightness $Y_M$ of the mucous membrane.

The color of blood vessels is respective values of RGB of the pixels representing the blood vessels. The change in the color of the blood vessels is a difference or a ratio between respective maximum and minimum values of respective RGB values of pixels representing blood vessels. For example, the ratio of a maximum value and a minimum value of pixel values of the B pixels representing the blood vessels, the ratio of a maximum value and a minimum value of pixel values of the G pixels, or the ratio of a maximum value and a minimum value of pixel values of the R pixels represents the change in the color of the blood vessels. Of course, the color of the blood vessels and the change in the color of the blood vessels may be calculated regarding respective values of cyan, magenta, yellow, green, and the like through conversion into complementary colors.

The degree of meandering of the blood vessels is blood vessel information representing the breadth of a range where blood vessels meander and travel. The degree of meandering of blood vessels is, for example, the area (number of pixels) of a minimum oblong shape including blood vessels from which the degree of meandering is calculated. Additionally, the ratio of the length of a blood vessel to a linear distance between a start point and an end point of the blood vessel may be used as the degree of meandering of blood vessels.

The blood concentration of the blood vessels is blood vessel information proportional to the amount of hemoglobin contained in the blood flowing through a blood vessel. Since the ratio (G/R) of the pixel values of the G pixels to the pixel values of the R pixels representing the blood vessels is proportional to the amount of hemoglobin, the blood concentration can be calculated for each pixel by calculating the value of G/R.

The degree of oxygen saturation of blood vessels is the amount of oxyhemoglobin to the total amount of hemoglobin (the total amount of oxyhemoglobin and reduced hemoglobin). The degree of oxygen saturation can be calculated using an endoscopic image obtained by imaging the observation target with light (for example, blue light with a wavelength of about 470±10 nm) of a specific large wavelength range where a difference between the light absorption coefficients of the oxyhemoglobin and the reduced hemoglobin is large. Since the pixel values of the B pixels representing the blood vessels have a correlation with the degree of oxygen saturation in a case where the blue light with a wavelength of about 470±10 nm is used, the degree of oxygen saturation of the respective pixels representing the blood vessels can be calculated by using a table or the like in which the pixel values of the B pixels are associated with the degree of oxygen saturation.

The artery proportion is the proportion of the number of pixels of arteries to the number of pixels of all blood vessels. Similarly, the vein proportion is the proportion of the number of pixels of veins to the number of pixels of all blood vessels. The arteries and the veins can be distinguished from each other depending on the degree of oxygen saturation. For example, if blood vessels with the degree of oxygen saturation of 70% or more are the arteries, and blood vessels with the degree of oxygen saturation of less than 70% are the veins, extracted blood vessels are divided into the arteries and the veins. Thus, the percentage of the above arteries and the percentage of the veins can be calculated.

The concentration of the input coloring agent is the concentration of the coloring agent dispersed onto the observation target, or the coloring agent injected into a blood vessel by intravenous injection. The concentration of the input coloring agent is calculated, for example, in the ratio of the pixel values of the color of the coloring agent to the pixel values of pixels other than the color of the coloring agent. For example, in a case where a coloring agent that gives blue color is input, the ratio B/G of the Bs image signal and the Gs image signal, the ratio B/R of the Bs image signal and the Rs image signal, or the like represents the concentration of the coloring agent fixed (or temporarily adhered) to the observation target.

The traveling pattern of the blood vessels is blood vessel information on the traveling direction of blood vessels. The traveling pattern of blood vessels is, for example, the average angle (traveling direction) of blood vessels to an arbitrarily set reference line, the dispersion (variations in traveling direction) of angles that blood vessels make with respect to the arbitrarily set reference line, or the like.

The blood flow rate (also referred to blood flow velocity) of the blood vessels is the number of red cells which pass through a blood vessel per unit time. For example, in a case where an ultrasonic probe is used together via a forceps channel or the like of the endoscope 12, the blood flow rate of blood vessels can be calculated by calculating the Doppler shift frequency of the respective pixels representing the blood vessels of the endoscopic image, using signals obtained by the ultrasonic probe.

Second Embodiment

In a second embodiment, the observation target is illuminated using a laser light source and a fluorescent body instead of the four-color LEDs 20a to 20d illustrated in the above first embodiment. In the following, only portions different from the first embodiment will be described, and description of substantially the same portions as those of the first embodiment will not be repeated.

Figure 17:
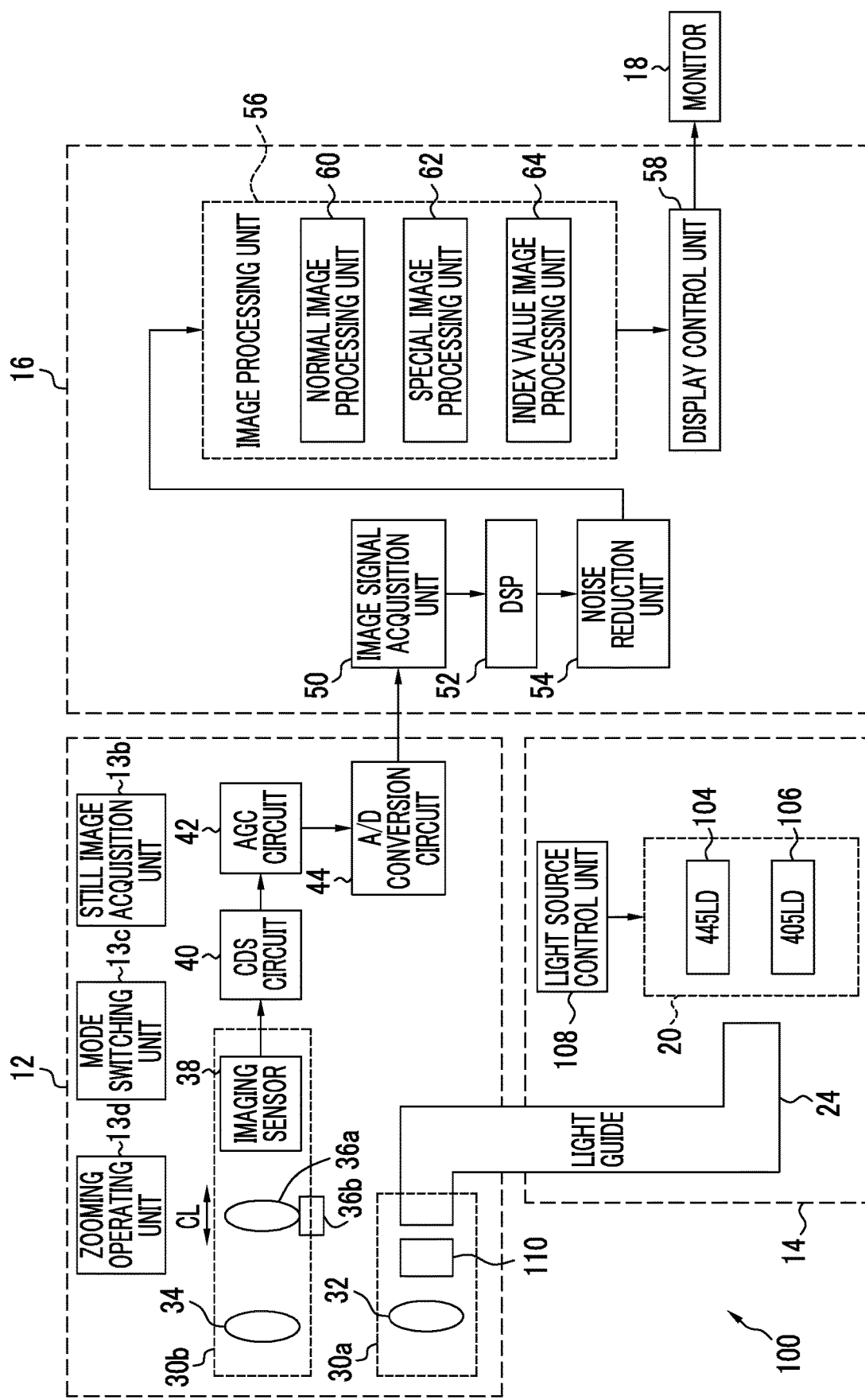
FIG. 17 is a block diagram illustrating functions of an endoscope system of a second embodiment.

As illustrated in FIG. 17, in the endoscope system 100 of the second embodiment, in the light source 20 of the light source device 14, a blue laser light source that emits blue laser light having a center wavelength of 445±10 nm (written as "445LD"; LD represents Laser Diode) 104 and a blue-violet laser light source (written as "405LD") 106 that emits blue-violet laser light having a center wavelength of 405±10 nm are provided instead of the four-color LEDs 20a to 20d. The light emission from semiconductor light-emitting elements of the respective light sources 104 and 106 are individually controlled by a light source control unit 108, and the quantity-of-light ratio of the emitted light of the blue laser light source 104 and the emitted light of the blue-violet laser light source 106 is changeable.

The light source control unit 108 turns on the blue laser light source 104 in the case of the normal mode. In contrast, in the case of the special mode or the index value display mode, both the blue laser light source 104 and the blue-violet laser light source 106 are turned on, and the light emission ratio of the blue laser light is controlled to become larger than the light emission ratio of the blue-violet laser light.

In addition, it is preferable that the half-width of the blue laser light or the blue-violet laser light is about +10 nm. Additionally, as the blue laser light source 104 and the blue-violet laser light source 106, broad area type InGaN-based laser diodes can be utilized, and InGaNAs-based laser diodes or GaNAsb-based laser diodes can also be used. Additionally, a configuration using a light emitter, such as a light emitting diode, may be adopted as the above light source.

The illumination optical system 30a is provided with a fluorescent body 110 that the blue laser light or the blue-violet laser light from the light guide 24 enters in addition to the illumination lens 32. The fluorescent body 110 is excited by the blue laser light to emit fluorescence. Additionally, a portion of the blue laser light is transmitted through the fluorescent body 110 without exciting the fluorescent body 110. The blue-violet laser light is transmitted through the fluorescent body 110 without exciting the fluorescent body 110. The inside of the body of the observation target is illuminated with the light emitted from the fluorescent body 110 via the illumination lens 32.

Figure 18:
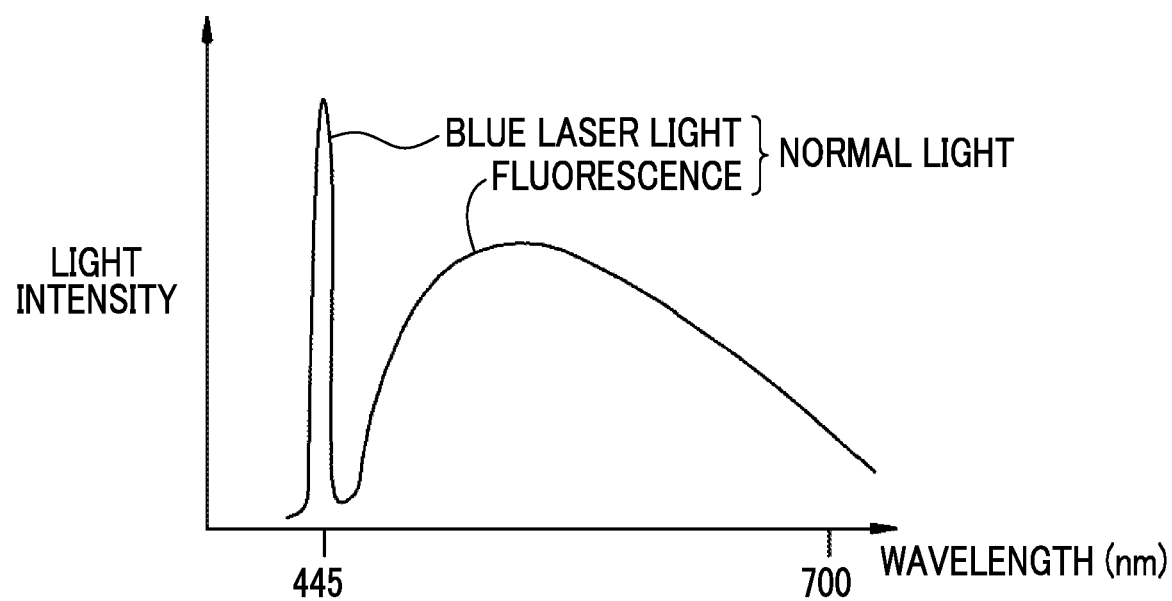
FIG. 18 is a graph illustrating a spectroscopic spectrum of normal light of the second embodiment.

Here, in the normal mode, mainly, the blue laser light enters the fluorescent body 110. Therefore, the broadband light for normal mode, which is obtained by combining the blue laser light with the fluorescence excited and emitted from the fluorescent body 110 due to the blue laser light as illustrated in FIG. 18, is illuminated to the observation target as the normal light. By imaging the observation target illuminated with the normal light by the imaging sensor 38, the normal image including the Bc image signal, the Gc image signal, and the Rc image signal is obtained.

Figure 19:
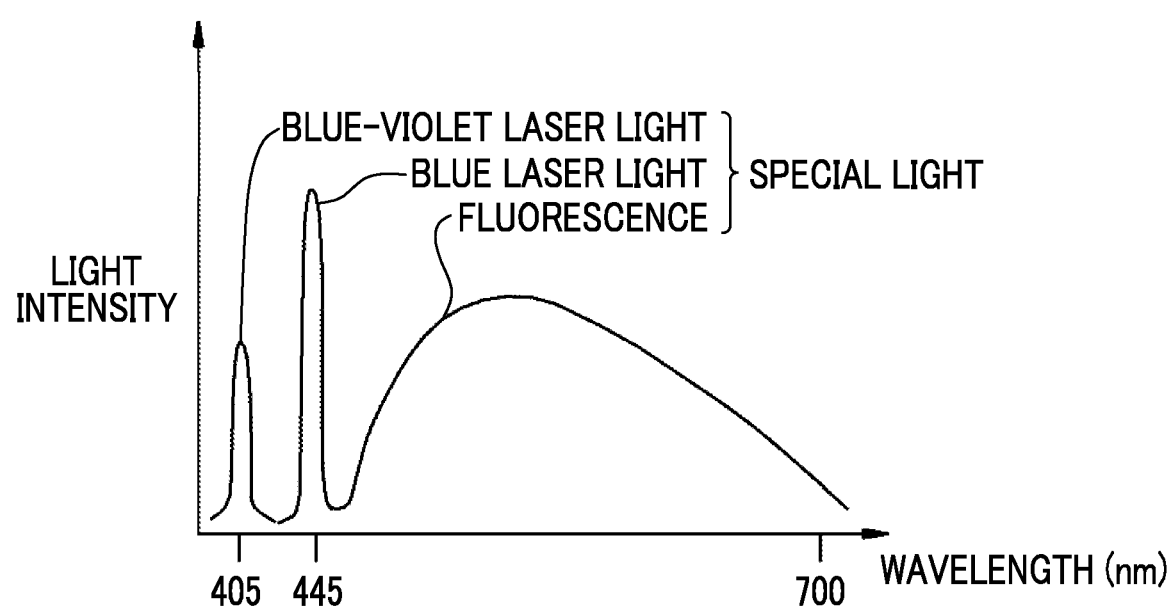
FIG. 19 is a graph illustrating a spectroscopic spectrum of special light of the second embodiment.

On the other hand, in the special mode or the index value display mode, the blue-violet laser light and the blue laser light enter the fluorescent body 110. Therefore, the broadband light for special mode, which is obtained by combining the blue-violet laser light, the blue laser light, and the fluorescence excited and emitted from the fluorescent body 110 due to the blue laser light together as illustrated in FIG. 19, is illuminated to the observation target as the special light. By imaging the observation target illuminated with the special light by the imaging sensor 38, the special image including the Bs image signal, the Gs image signal, and the Rs image signal is obtained. Additionally, in the index value display mode, the observation target illuminated with the special light is imaged by the imaging sensor 38, and Bs image signal, Gs image signal, and Rs image signal are acquired, the index values are calculated on the basis of the three image signals, and the index value image is generated.

In addition, as the fluorescent body 110, it is preferable to use those configured to include a plurality of types of fluorescent bodies (for example, a YAG-based fluorescent body or fluorescent bodies, such as BAM ($BaMgAl_{10}O_{17}$)) that absorb a portion of the blue laser light and are excited to emit light in green to yellow. As in the present configuration example, in a case where the semiconductor light-emitting elements are used as the excitation light sources of the fluorescent body 110 high-sensitive white light with a high luminous efficiency can be acquired, the intensity of the white light can be easily adjusted, and changes in color temperature and chromaticity of the white light can be suppressed to be small.

Third Embodiment

In the third embodiment, the observation target is illuminated using a white light source, such as a xenon lamp, and the rotation filter instead of the four-color LEDs 20a to 20d. Additionally, the observation target may be imaged by a monochrome imaging sensor instead of the color imaging sensor 38. In the following, only portions different from the first embodiment will be described, and description of substantially the same portions as those of the first embodiment will not be repeated.

Figure 20:
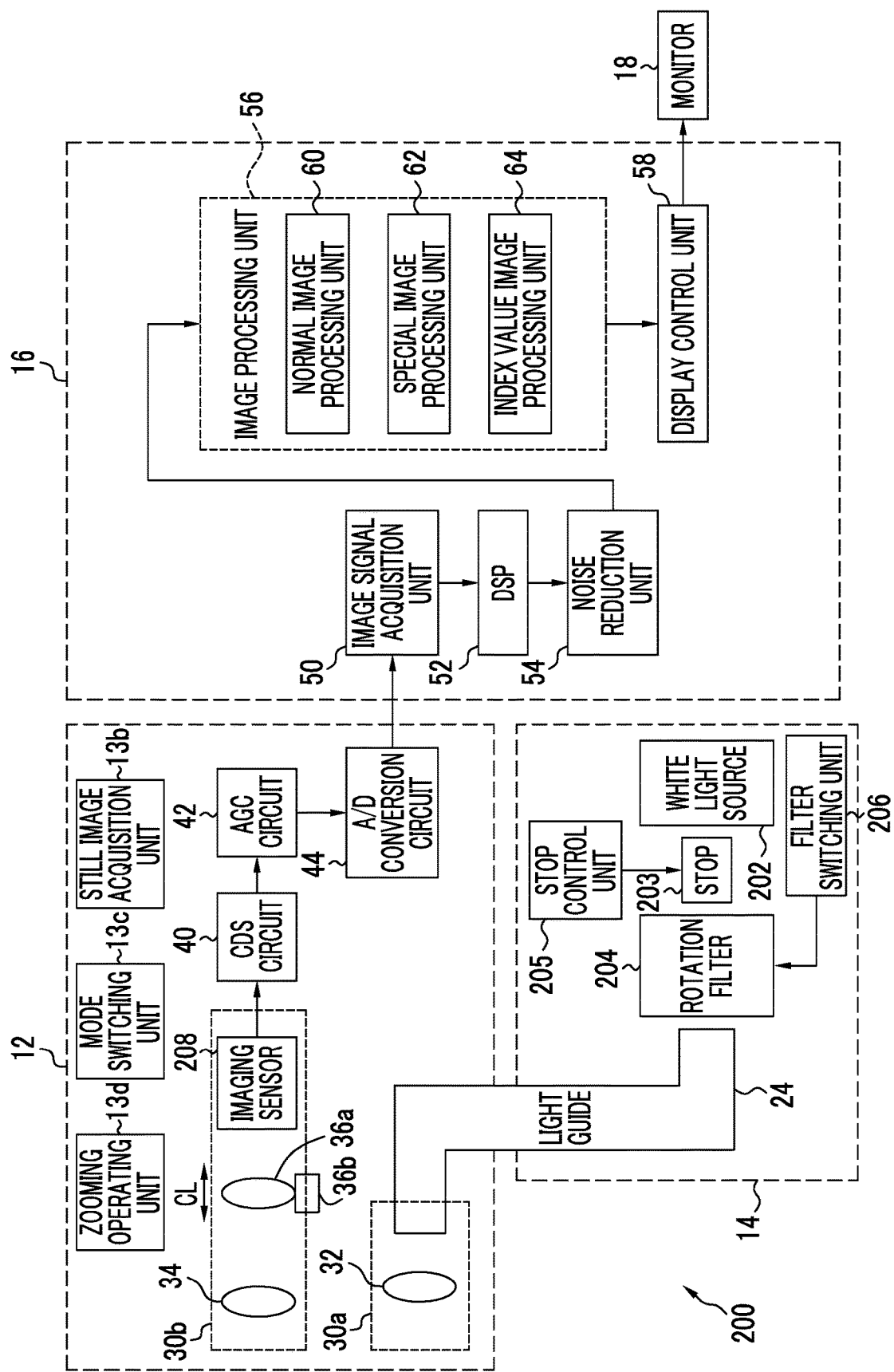
FIG. 20 is a block diagram illustrating functions of an endoscope system of a third embodiment.

In an endoscope system 200 illustrated in FIG. 20, in the light source device 14, a white light source 202, a rotation filter 204, and a filter switching unit 206 are provided instead of the respective LEDs 20a to 20d of the endoscope system 10. Additionally, the imaging optical system 30b is provided with a monochrome imaging sensor 208, which is not provided with a color filter, instead of the color imaging sensor 38. Additionally, a stop 203 is provided between the white light source 202 and the rotation filter 204, and the area of an opening of the stop 203, is adjusted by a stop control unit 205.

The white light source 202 is a xenon lamp, a white LED, or the like, and emits white light of which the wavelength range ranges from blue to red. The rotation filter 204 comprises a normal mode filter 210 that is provided on an inner side closest to a rotation axis thereof, and a special mode or index value display mode filter 212 provided outside the normal mode filter 210 (refer to FIG. 21).

The filter switching unit 206 moves the rotation filter 204 in a radial direction. Specifically, the filter switching unit 206 inserts the normal mode filter 210 into a white light path in a case where the normal mode is set by the mode switching unit 13c. Specifically, the filter switching unit 206 inserts the special mode or index value display mode filter 212 into the white light path in a case where the special mode or the index value display mode is set by the mode switching unit 13c.

Figure 21:
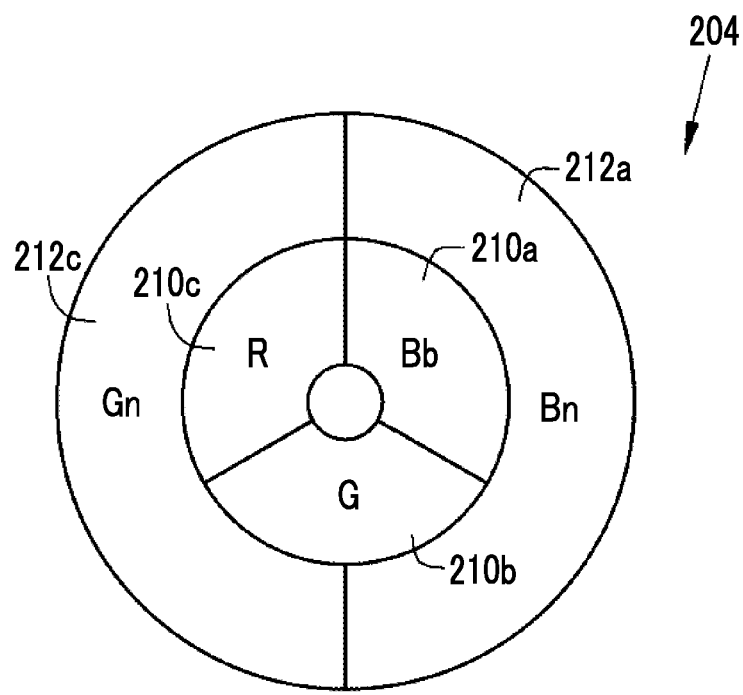
FIG. 21 is a plan view of a rotation filter.

As illustrated in FIG. 21, a Bb filter 210*a*, a G filter 210*b*, and an R filter 210*c* are provided in the circumferential direction in the normal mode filter 210. The Bb filter 210*a* transmits the broadband blue light Bb, which has a wavelength range of 400 to 500 nm, in the white light. The G filter 210*b* transmits the green light G in the white light. The R filter 210*c* transmits the red light R in the white light. Hence, in the normal mode, as the rotation filter 204 rotates, the broadband blue light Bb, the green light G, and the red light R are successively radiated toward the observation target as the normal light.

A Bn filter 212*a* and a Gn filter 212*b* are provided in the circumferential direction in the special mode or index value display mode filter 212. The Bn filter 212*a* transmits narrowband blue light Bn of 400 to 450 nm in the white light. The Gn filter 212*b* transmits narrowband green light Gn of 530 to 570 nm in the white light. Hence, in the special mode, as the rotation filter 204 rotates, the narrowband blue light and the narrowband green light are successively radiated toward the observation target as the special light.

In the endoscope system 200, in the normal mode, whenever the observation target is illuminated with the broadband blue light Bb, the green light G, and the red light R, respectively, the observation target is imaged by the monochrome imaging sensor 208. As a result, the Bc image signal is obtained at the time of the illumination with the broadband blue light Bb, the Gc image signal is obtained at the time of the illumination with the green light G, and the Rc image signal is obtained at the time of the illumination with the red light R. The normal image is constituted of the Bn image signal, the Gc image signal, and the Rc image signal.

In the special mode, the observation target is imaged by the monochrome imaging sensor 208 whenever the observation target is illuminated with narrowband blue light Bn and the narrowband green light Gn, respectively. Accordingly, the Bn image signal is obtained at the time of the illumination with the narrowband blue light Bn, and the Gn image signal is obtained at the time of the irradiation with the narrowband green light Gn. The special image is constituted of the Bn image signal and the Gn image signal. Additionally, in the case of the index value display modes, the calculation of the index values and the generation of the index value image are performed on the basis of the Bn image signal obtained at the time of the irradiation with the narrowband blue light Bn, and the Gn image signal obtained at the time of the illumination with the narrowband green light Gn.

EXPLANATION OF REFERENCES

10: endoscope system
12: endoscope
12*a*: insertion part
12*b*: operating part
12*c*: bending part
12*d*: distal end part
13*a*: angle knob
13*b*: still image acquisition unit
13*c*: mode switching unit
13*d*: zooming operating unit
14: light source device
16: processor device
18: monitor
19: console
20: light source
20*a*: V-LED
20*b*: B-LED
20*c*: G-LED
20*d*: R-LED
22: light source control unit
23: wavelength cutoff filter
24: light guide
30*a*: illumination optical system
30*b*: imaging optical system
32: illumination lens
34: objective lens
36: magnifying optical system
36*a*: zoom lens
36*b*: lens drive unit
38: imaging sensor
40: CDS circuit
42: AGC circuit
44: A/D conversion circuit
50: image signal acquisition unit
52: DSP
54: noise reduction unit
56: image processing unit
58: display control unit
60: normal image processing unit
62: special image processing unit
64: index value image processing unit
68: lesion diagnostic pattern setting unit
70: index value calculation unit
72: index value determination unit
74: index value arithmetic processing unit
74*a*: processing order storage unit
76: index value image generation unit
78: mucous membrane determination unit
83: blood vessel information calculation unit
100: endoscope system
104: blue laser light source
106: blue-violet laser light source
108: light source control unit
110: fluorescent body
200: endoscope system
202: white light source
204: rotation filter
205: stop control unit
206: filter switching unit
208: imaging sensor
210: normal mode filter
210*a*: Bb filter
210*b*: G filter
210*c*: R filter
212: special mode or index value display mode filter
212*a*: Bn filter
212*b*: Gn filter

What is claimed is:

1. A processor device comprising:
a processor; and
a memory, configured to store a plurality of processing orders, each processing order relating to a particular range of a first index value among a plurality of ranges of the first index value, a particular type of vascular pattern among a plurality of types of vascular patterns, and a particular second index value to be calculated among a plurality of second index values to be calculated,
wherein the processor is configured to:
acquire an image obtained by imaging an observation target including a structure; and
perform an index value calculation process of calculating the first index value and only one of the plurality of second index values by indexing a property of the structure on the basis of the image according to a processing order;

wherein the processor is configured to:

calculate the first index value from the image, determine which particular range the calculated first index value falls within, select the processing order from among the plurality of processing orders related to the determined range, determine the structure as including the particular type of vascular pattern related to the selected processing order, and only calculate the second index value related to the selected processing order.

2. The processor device according to claim 1, wherein the processor further performs a mucous membrane determination process of determining a state of a mucous membrane on the basis of an index value for mucous membrane determination, and performs a control so as to repeat the index value calculation process until a calculation of the index value for mucous membrane determination is completed.

3. The processor device according to claim 2, wherein the state of the mucous membrane includes at least one of a particular type of vascular pattern, a progress of a specific lesion, or a normal mucous membrane state.

4. The processor device according to claim 3, wherein the structure includes a blood vessel structure or a mucous membrane structure.

5. The processor device according to claim 3, wherein the processor acquires a multi-frame image obtained by imaging the observation target in different frames, the multi-frame image including an image for index value calculation.

6. The processor device according to claim 3, wherein the processing order is preset on the basis of medical knowledge for a specific lesion.

7. An endoscope system comprising:

the processor device according to claim 3;

a display that displays an index value image obtained by imaging the first index value and the second index value, wherein the processor performs a display control according to the processing order so that the first index value is displayed on the display and then the second index value is displayed on the display.

8. The processor device according to claim 2, wherein the structure includes a blood vessel structure or a mucous membrane structure.

9. The processor device according to claim 2, wherein the processor acquires a multi-frame image obtained by imaging the observation target in different frames, the multi-frame image including an image for index value calculation.

10. The processor device according to claim 2, wherein the processing order is preset on the basis of medical knowledge for a specific lesion.

11. An endoscope system comprising:

the processor device according to claim 2;

a display that displays an index value image obtained by imaging the first index value and the second index value, wherein the processor performs a display control according to the processing order so that the first index value is displayed on the display and then the second index value is displayed on the display.

12. An endoscope system comprising:

the processor device according to claim 2; and a display that displays a result of the mucous membrane determination process.

13. The processor device according to claim 1, wherein the structure includes a blood vessel structure or a mucous membrane structure.

14. The processor device according to claim 13, wherein the processor acquires a multi-frame image obtained by imaging the observation target in different frames, the multi-frame image including an image for index value calculation.

15. The processor device according to claim 13, wherein the processing order is preset on the basis of medical knowledge for a specific lesion.

16. The processor device according to claim 1, wherein the processor acquires a multi-frame image obtained by imaging the observation target in different frames, the multi-frame image including an image for index value calculation.

17. The processor device according to claim 1, wherein the processing order is preset on the basis of medical knowledge for a specific lesion.

18. An endoscope system comprising:

the processor device according to claim 1;

a display that displays an index value image obtained by imaging the first index value and the second index value, wherein the processor performs a display control according to the processing order so that the first index value is displayed on the display and then the second index value is displayed on the display.

19. A method of operating a processor device comprising:

acquiring an image obtained by imaging an observation target including a structure, using a processor; and performing an index value calculation process of calculating a first index value and only one of second index values by indexing a property of the structure on the basis of the image according to a processing order, using the processor;

storing a plurality of processing orders, using a memory, each processing order relating to a particular range of the first index value among a plurality of ranges of the first index value, a particular type of vascular pattern among a plurality of types of vascular patterns, and a particular second index value to be calculated among a plurality of the second index values to be calculated, wherein the step of performing the index value calculation process of calculating the first index value and the only one of the plurality of second index values by indexing the property of the structure on the basis of the image according to the processing order comprises:

calculate the first index value from the image;

determine which particular range the calculated first index value falls within;

select the processing order from among the plurality of processing orders related to the determined range;

determine the structure as including the particular type of vascular pattern related to the selected processing order; and only calculate the second index value related to the selected processing order.

* * * * *